(12) United States Patent
Nakamura et al.

(10) Patent No.: US 7,514,597 B2
(45) Date of Patent: Apr. 7, 2009

(54) GLYCOSYLTRANSFERASE GENE

(75) Inventors: Noriko Nakamura, Kyoto (JP); Yuko Fukui, Osaka (JP); Eiichiro Ono, Shiga (JP); Yoshikazu Tanaka, Shiga (JP); Hiroaki Okuhara, Osaka (JP)

(73) Assignee: Suntory Limited, Osaka-shi (JP)

( * ) Notice: Subject to any disclaimer, the term of this patent is extended or adjusted under 35 U.S.C. 154(b) by 181 days.

(21) Appl. No.: 10/524,842

(22) PCT Filed: Aug. 20, 2003

(86) PCT No.: PCT/JP03/10500

§ 371 (c)(1),
(2), (4) Date: Sep. 14, 2005

(87) PCT Pub. No.: WO2004/018682

PCT Pub. Date: Mar. 4, 2004

(65) Prior Publication Data

US 2006/0174377 A1    Aug. 3, 2006

(30) Foreign Application Priority Data

Aug. 20, 2002  (JP) ............................. 2002-239743
Mar. 26, 2003  (JP) ............................. 2003-085452

(51) Int. Cl.
*C12N 15/29* (2006.01)
*C12N 15/52* (2006.01)
*C12N 15/82* (2006.01)
*A01H 5/00* (2006.01)

(52) U.S. Cl. .................. 800/283; 800/298; 800/232; 435/69.1; 435/419; 435/468; 530/370

(58) Field of Classification Search .................. None
See application file for complete search history.

(56) References Cited

FOREIGN PATENT DOCUMENTS

EP       1 072 684    1/2001
WO       01/92509     12/2001

OTHER PUBLICATIONS

Forkmann G, et al. Biochemical genetics; Jun. 1980, vol. 18, No. 5-6, pp. 519-527.*
Kishimoto S. et al. Phytochemistry 2004; vol. 65, pp. 2781-2787.*
Ishida, Madoka et al. "Isolation of cDNA for the chalcone 2'-glucosyltransferase gene and its expression profile in carnation flowers", Plant Cell Physiol., vol. 44, supplement, p. s158, 2003.
Yamazaki, Mami et al. "Molecular Cloning and Biochemical Characterization of a Novel Anthocyanin 5-O-Glucosyltransferase by mRNA Differential Display for Plant Forms Regarding Anthocyanin", Journal of Biological Chemistry, vol. 274, No. 11, pp. 7405-7411, 1999.
Li, Yi et al. "Phylogenetic Analysis of the UDP-glycosyltransferase Multigene Family of *Arabidopsis thaliana*", Journal of Biological Chemistry, vol. 276, No. 6, pp. 4338-4343, 2001.
Vogt, Thomas. "Substrate specificity and sequence analysis define a polyphyletic orgin of betanidin 5- and 6-O-glucosyltransferase from *Dorotheanthus bellidiformis*", Planta, vol. 214, No. 3, pp. 492-495, 2002.
Tanaka, Yoshikazu et al. "Metabolic Engineering to Modify Flower Color", Plant Cell Physiol., vol. 39, No. 11, pp. 1119-1126, 1998.
Forkmann, Gert et al. "Metabolic engineering and applications of flavonoids", Current Opinion in Biotechnology, vol. 12, pp. 155-160, 2001.
"Biohorti I", pp. 49-57, Seibundo Shinkosha, 1990.
Forkmann, Gert et al. "1.26 Biosynthesis of Flavonoids", Comprehensive Natural Products Chemistry, vol. 1, pp. 713-748, 1999.
Nakayama, T. et al. "Aureusidin Synthase: A Polyphenol Oxidase Homolog Responsible for Flower Coloration", Science, vol. 290, pp. 1163-1166, 2000.
Davies, Kevin et al. "Biotechnology of Ornamental Plants", Biotechnology in Agriculture Series, No. 16, pp. v, 260-294, 1997.
Hrazdina, Geza et al. "Subcellular Localization of Enzymes of Anthocyanin Biosynthesis in Protoplasts", Phytochemistry, vol. 17, pp. 53-56, 1978.
Davies, Kevin et al. "Production of yellow colour in flowers: redirection of flavonoid biosynthesis in Petunia", The Plant Journal, vol. 13, No. 2, pp. 259-266, 1998.
Vogt, Thomas et al. "Glycosyltransferases in plant natural product synthesis: characterization of a supergene family", Trends in Plant Science, vol. 5, No. 9, pp. 380-386, 2000.
Yamazaki, Mami et al. "Two flavonoid glucosyltransferases from *Petunia hybrida*: molecular cloning, biochemical properties and developmentally regulated expression", Plant Molecular Biology, vol. 48, pp. 401-411, 2002.

* cited by examiner

*Primary Examiner*—Russell Kallis
(74) *Attorney, Agent, or Firm*—Oblon, Spivak, McClelland, Maier & Neustadt, P.C.

(57) ABSTRACT

The present invention provides an enzyme which catalyzes a reaction to transfer sugar to a hydroxyl group at position 2' of chalcones and a gene thereof, and preferably an enzyme which catalyzes a reaction to transfer glucose to a hydroxyl group at position 2' of the chalcones. Furthermore, the invention provides a plant whose flower color has been changed using the glycosyltransferase. Using probes corresponding to conservative regions of the glycosyltransferase, some tens of glycosyltransferase genes having nucleotide sequences corresponding to the conservative regions were cloned from flower petal cDNA libraries of carnation and the like. Furthermore, each of the glycosyltransferase genes was expressed in *Escherichia coli*, activity to transfer glucose to position 2' of the chalcone, i.e., the glycosyltransferase activity at position 2' of chalcone was confirmed in an extract solution of the *Escherichia coli*, and it was confirmed that cloned genes encoded the glycosyltransferase at position 2'.

9 Claims, 2 Drawing Sheets

```
SEQUENCE LISTING

<160> NUMBER OF SEQ ID NOS: 60

<210> SEQ ID NO 1
<211> LENGTH: 1751
<212> TYPE: DNA
<213> ORGANISM: Dianthus caryophyllus cv. light cream candle
<220> FEATURE:
<221> NAME/KEY: CDS
<222> LOCATION: (43)..(1509)

<400> SEQUENCE: 1
ctcgtctaat aaactcgaaa agtttattaa gcgagttcaa ac atg agc aaa gca         54
                                                Met Ser Lys Ala
                                                 1 ccg ttc gag ttg gta ttc atc cca act ccg gct gta ggt cac att ata       102
Pro Phe Glu Leu Val Phe Ile Pro Thr Pro Ala Val Gly His Ile Ile
 5                  10                  15                  20 tcg acc gtt caa ctc gct aaa tta att ctt aat aaa aac gat tta atc       150
Ser Thr Val Gln Leu Ala Lys Leu Ile Leu Asn Lys Asn Asp Leu Ile
                25                  30                  35 ttt gtt tct att tac gtc atc aac ttt tct atg cac tct tct aaa gtc       198
```

-continued

```
                Phe Val Ser Ile Tyr Val Ile Asn Phe Ser Met His Ser Ser Lys Val
                             40                  45                  50 aac gcc tac att gac tcc cag tca cgt gat aac ccg tac ccg acc cgt        246
Asn Ala Tyr Ile Asp Ser Gln Ser Arg Asp Asn Pro Tyr Pro Thr Arg
         55                  60                  65 ctg act ttc gta tcc ctt ccg ctc ctg cca gac atg ttc gac ccg ttt        294
Leu Thr Phe Val Ser Leu Pro Leu Leu Pro Asp Met Phe Asp Pro Phe
 70                  75                  80 tct ccc act caa ttt act gct gcc atc gac ctc cac aag ccg ttc gtt        342
Ser Pro Thr Gln Phe Thr Ala Ala Ile Asp Leu His Lys Pro Phe Val
 85                  90                  95                 100 aag cag gcg gtt gag gac cga gtt cgg gac ggg ctt ccc aag ccc gtc        390
Lys Gln Ala Val Glu Asp Arg Val Arg Asp Gly Leu Pro Lys Pro Val
                    105                 110                 115 ggg ttc gtc ctc gac atg ttt tgc acc tca atg gcg gat att gcc aac        438
Gly Phe Val Leu Asp Met Phe Cys Thr Ser Met Ala Asp Ile Ala Asn
                    120                 125                 130 gag ttg agt gta ccg tcg tac gtt tac ttt act tcg ggt gca aat ctt        486
Glu Leu Ser Val Pro Ser Tyr Val Tyr Phe Thr Ser Gly Ala Asn Leu
                    135                 140                 145 ctg aat ttc aca ttc ttt gct cag tcg ttc gca gac gat cat caa gaa        534
Leu Asn Phe Thr Phe Phe Ala Gln Ser Phe Ala Asp Asp His Gln Glu
150                 155                 160 atc gat cct gcg gtt gag ttt agt agg ccg gaa ttt tca gcg gtt gtg        582
Ile Asp Pro Ala Val Glu Phe Ser Arg Pro Glu Phe Ser Ala Val Val
165                 170                 175                 180 ccc ggg ttt aag aac ccg gtc aca agc gcc gct att cct gcg gtg ttt        630
Pro Gly Phe Lys Asn Pro Val Thr Ser Ala Ala Ile Pro Ala Val Phe
                    185                 190                 195 caa gag aaa aac ggg tgc gag ttg ctc ctc ggc ttt gcg agg aag ttt        678
Gln Glu Lys Asn Gly Cys Glu Leu Leu Leu Gly Phe Ala Arg Lys Phe
                    200                 205                 210 aga gaa atg aaa ggt att ttg atg aat acc tat gtg gaa tta gaa aac        726
Arg Glu Met Lys Gly Ile Leu Met Asn Thr Tyr Val Glu Leu Glu Asn
                    215                 220                 225 ttc ggt ata cat gcg tta atg aat ggt gat ggt aag aaa att ccg cct        774
Phe Gly Ile His Ala Leu Met Asn Gly Asp Gly Lys Lys Ile Pro Pro
230                 235                 240 att tat ccc gtg ggc ccc att ttg gag ctc ggc aac acg agt act ggt        822
Ile Tyr Pro Val Gly Pro Ile Leu Glu Leu Gly Asn Thr Ser Thr Gly
245                 250                 255                 260 ggg tct gac aat agt aag gac gtg tcc gta att cag tgg ctt gat ggt        870
Gly Ser Asp Asn Ser Lys Asp Val Ser Val Ile Gln Trp Leu Asp Gly
                    265                 270                 275 caa ccg aag tca tca gtg gtg ttt ctg tgt ttt gga agt atg gga agt        918
Gln Pro Lys Ser Ser Val Val Phe Leu Cys Phe Gly Ser Met Gly Ser
                    280                 285                 290 ttt gat gaa gaa caa att aaa gag ata gcg atc ggt cta gaa cgg tcg        966
Phe Asp Glu Glu Gln Ile Lys Glu Ile Ala Ile Gly Leu Glu Arg Ser
                    295                 300                 305 gga caa cgg tat tta tgg gcc tta cgt aaa ccg cct tct tca gga aag       1014
Gly Gln Arg Tyr Leu Trp Ala Leu Arg Lys Pro Pro Ser Ser Gly Lys
                    310                 315                 320 gta ggg gtc cct agt gag agt gag gcg ttc tta gag gcc ctt cct gag       1062
Val Gly Val Pro Ser Glu Ser Glu Ala Phe Leu Glu Ala Leu Pro Glu
325                 330                 335                 340 ggg ttc att gat cgt acg atc agt ggt aag ggg aaa atc ata gcg tgg       1110
Gly Phe Ile Asp Arg Thr Ile Ser Gly Lys Gly Lys Ile Ile Ala Trp
                    345                 350                 355
```

```
gcc ccg cag gtt gag gta tta gcc cac cct gcc gta gga ggg ttc gtg    1158
Ala Pro Gln Val Glu Val Leu Ala His Pro Ala Val Gly Gly Phe Val
        360                 365                 370 tta cac tgt ggg tgg aac tcg acg ttg gag agc ata tgg ttt ggg gtt    1206
Leu His Cys Gly Trp Asn Ser Thr Leu Glu Ser Ile Trp Phe Gly Val
    375                 380                 385 ccc atg gca act tgg cct att tat gcg gaa cag cag ctg aac gcg ttt    1254
Pro Met Ala Thr Trp Pro Ile Tyr Ala Glu Gln Gln Leu Asn Ala Phe
390                 395                 400 gag tta gta aag gag ttg gaa ttg gca att gaa ata agg atg gat tac    1302
Glu Leu Val Lys Glu Leu Glu Leu Ala Ile Glu Ile Arg Met Asp Tyr
405                 410                 415                 420 aaa acg gat ata gaa act caa aag gcg ggc ttc atg gta aag gcc gag    1350
Lys Thr Asp Ile Glu Thr Gln Lys Ala Gly Phe Met Val Lys Ala Glu
                425                 430                 435 gag ata gaa gaa gga att agg gca tta atg aat gtg gat gag acg atg    1398
Glu Ile Glu Glu Gly Ile Arg Ala Leu Met Asn Val Asp Glu Thr Met
                440                 445                 450 cgt gaa cga gtc aag acg atg agt gac tat ggc aaa aag gct ttg gaa    1446
Arg Glu Arg Val Lys Thr Met Ser Asp Tyr Gly Lys Lys Ala Leu Glu
        455                 460                 465 cga gga gga tcg tcc tat aat tat ttg gaa ttc ttc att ggg gat gtt    1494
Arg Gly Gly Ser Ser Tyr Asn Tyr Leu Glu Phe Phe Ile Gly Asp Val
    470                 475                 480 ttg agc aat att agt taaattaaat tccaagagag tggatgaaaa tttaaaaaaa    1549
Leu Ser Asn Ile Ser
485 aaatgataag ttattgctct ctgcaatcat gtacggagta attttttaaca tttactattg    1609 aatcggtttt tttttaattaa agcatagtgt taaatttact taggtacctc tatattgtaa    1669 atgaagaagt tgatgacgat ttgatgtcag atataaaata aatgaatgga gtaaaaaaaa    1729 aaaaaaaaaa aaaaaaaaaa aa                                            1751

<210> SEQ ID NO 2
<211> LENGTH: 489
<212> TYPE: PRT
<213> ORGANISM: Dianthus caryophyllus cv. light cream candle

<400> SEQUENCE: 2

Met Ser Lys Ala Pro Phe Glu Leu Val Phe Ile Pro Thr Pro Ala Val
1               5                   10                  15

Gly His Ile Ile Ser Thr Val Gln Leu Ala Lys Leu Ile Leu Asn Lys
            20                  25                  30

Asn Asp Leu Ile Phe Val Ser Ile Tyr Val Ile Asn Phe Ser Met His
        35                  40                  45

Ser Ser Lys Val Asn Ala Tyr Ile Asp Ser Gln Ser Arg Asp Asn Pro
    50                  55                  60

Tyr Pro Thr Arg Leu Thr Phe Val Ser Leu Pro Leu Leu Pro Asp Met
65                  70                  75                  80

Phe Asp Pro Phe Ser Pro Thr Gln Phe Thr Ala Ala Ile Asp Leu His
                85                  90                  95

Lys Pro Phe Val Lys Gln Ala Val Glu Asp Arg Val Arg Asp Gly Leu
            100                 105                 110

Pro Lys Pro Val Gly Phe Val Leu Asp Met Phe Cys Thr Ser Met Ala
        115                 120                 125

Asp Ile Ala Asn Glu Leu Ser Val Pro Ser Tyr Val Tyr Phe Thr Ser
    130                 135                 140
```

```
Gly Ala Asn Leu Leu Asn Phe Thr Phe Phe Ala Gln Ser Phe Ala Asp
145                 150                 155                 160

Asp His Gln Glu Ile Asp Pro Ala Val Glu Phe Ser Arg Pro Glu Phe
                165                 170                 175

Ser Ala Val Val Pro Gly Phe Lys Asn Pro Val Thr Ser Ala Ala Ile
            180                 185                 190

Pro Ala Val Phe Gln Glu Lys Asn Gly Cys Glu Leu Leu Leu Gly Phe
        195                 200                 205

Ala Arg Lys Phe Arg Glu Met Lys Gly Ile Leu Met Asn Thr Tyr Val
210                 215                 220

Glu Leu Glu Asn Phe Gly Ile His Ala Leu Met Asn Gly Asp Gly Lys
225                 230                 235                 240

Lys Ile Pro Pro Ile Tyr Pro Val Gly Pro Ile Leu Glu Leu Gly Asn
                245                 250                 255

Thr Ser Thr Gly Gly Ser Asp Asn Ser Lys Asp Val Ser Val Ile Gln
            260                 265                 270

Trp Leu Asp Gly Gln Pro Lys Ser Ser Val Val Phe Leu Cys Phe Gly
        275                 280                 285

Ser Met Gly Ser Phe Asp Glu Glu Gln Ile Lys Glu Ile Ala Ile Gly
290                 295                 300

Leu Glu Arg Ser Gly Gln Arg Tyr Leu Trp Ala Leu Arg Lys Pro Pro
305                 310                 315                 320

Ser Ser Gly Lys Val Gly Val Pro Ser Glu Ser Glu Ala Phe Leu Glu
                325                 330                 335

Ala Leu Pro Glu Gly Phe Ile Asp Arg Thr Ile Ser Gly Lys Gly Lys
            340                 345                 350

Ile Ile Ala Trp Ala Pro Gln Val Glu Val Leu Ala His Pro Ala Val
        355                 360                 365

Gly Gly Phe Val Leu His Cys Gly Trp Asn Ser Thr Leu Glu Ser Ile
370                 375                 380

Trp Phe Gly Val Pro Met Ala Thr Trp Pro Ile Tyr Ala Glu Gln Gln
385                 390                 395                 400

Leu Asn Ala Phe Glu Leu Val Lys Glu Leu Glu Leu Ala Ile Glu Ile
                405                 410                 415

Arg Met Asp Tyr Lys Thr Asp Ile Glu Thr Gln Lys Ala Gly Phe Met
            420                 425                 430

Val Lys Ala Glu Glu Ile Glu Glu Gly Ile Arg Ala Leu Met Asn Val
        435                 440                 445

Asp Glu Thr Met Arg Glu Arg Val Lys Thr Met Ser Asp Tyr Gly Lys
450                 455                 460

Lys Ala Leu Glu Arg Gly Gly Ser Ser Tyr Asn Tyr Leu Glu Phe Phe
465                 470                 475                 480

Ile Gly Asp Val Leu Ser Asn Ile Ser
                485

<210> SEQ ID NO 3
<211> LENGTH: 21
<212> TYPE: DNA
<213> ORGANISM: Artificial
<220> FEATURE:
<223> OTHER INFORMATION: Ipomoea purpurea 3GGT PN3GGTF

<400> SEQUENCE: 3
gaaatggtcg gattggctgg g                                          21
```

<210> SEQ ID NO 4
<211> LENGTH: 21
<212> TYPE: DNA
<213> ORGANISM: Artificial
<220> FEATURE:
<223> OTHER INFORMATION: Ipomoea purpurea 3GGT PN3GGTR

<400> SEQUENCE: 4
acctccaccc caactttcag g                                     21

<210> SEQ ID NO 5
<211> LENGTH: 21
<212> TYPE: DNA
<213> ORGANISM: Artificial
<220> FEATURE:
<223> OTHER INFORMATION: Gentiana scabra 3GT GT3GTF

<400> SEQUENCE: 5
tgcctcaaat ggcttcaaac t                                     21

<210> SEQ ID NO 6
<211> LENGTH: 20
<212> TYPE: DNA
<213> ORGANISM: Artificial
<220> FEATURE:
<223> OTHER INFORMATION: Gentiana scabra 3GT GT3GTR

<400> SEQUENCE: 6
ccacctttca ccccaacccc                                       20

<210> SEQ ID NO 7
<211> LENGTH: 21
<212> TYPE: DNA
<213> ORGANISM: Artificial
<220> FEATURE:
<223> OTHER INFORMATION: Verbena hydrida 5GT H5GTF

<400> SEQUENCE: 7
tgcctcgaat ggttgagcac g                                     21

<210> SEQ ID NO 8
<211> LENGTH: 18
<212> TYPE: DNA
<213> ORGANISM: Artificial
<220> FEATURE:
<223> OTHER INFORMATION: Verbena hydrida 5GT H5GTR

<400> SEQUENCE: 8
ctctcactct cacacccg                                         18

<210> SEQ ID NO 9
<211> LENGTH: 21
<212> TYPE: DNA
<213> ORGANISM: Artificial
<220> FEATURE:
<223> OTHER INFORMATION: Scutellaria baicalensis GT SBGTF

<400> SEQUENCE: 9
cacgaatgct tagcatggct c                                     21

<210> SEQ ID NO 10
<211> LENGTH: 21
<212> TYPE: DNA
<213> ORGANISM: Artificial
<220> FEATURE:
<223> OTHER INFORMATION: Scutellaria baicalensis GT SBGTR

<400> SEQUENCE: 10
cttattgccc actgaaaccc c                                                        21

<210> SEQ ID NO 11
<211> LENGTH: 22
<212> TYPE: DNA
<213> ORGANISM: Artificial
<220> FEATURE:
<223> OTHER INFORMATION: T170-NcoI PCR primer

<400> SEQUENCE: 11
agttcaacca tgggcaaagc ac                                                       22

<210> SEQ ID NO 12
<211> LENGTH: 17
<212> TYPE: DNA
<213> ORGANISM: Artificial
<220> FEATURE:
<223> OTHER INFORMATION: M13M4 PCR primer

<400> SEQUENCE: 12
gttttcccag tcacgac                                                             17

<210> SEQ ID NO 13
<211> LENGTH: 459
<212> TYPE: PRT
<213> ORGANISM: Ipomoea purpurea

<400> SEQUENCE: 13

Met Gly Ser Gln Ala Thr Thr Tyr His Met Ala Met Tyr Pro Trp Phe
1               5                   10                  15

Gly Val Gly His Leu Thr Gly Phe Phe Arg Leu Ala Asn Lys Leu Ala
            20                  25                  30

Gly Lys Gly His Arg Ile Ser Phe Leu Ile Pro Lys Asn Thr Gln Ser
        35                  40                  45

Lys Leu Glu Ser Phe Asn Leu His Pro His Leu Ile Ser Phe Val Pro
    50                  55                  60

Ile Val Val Pro Ser Ile Pro Gly Leu Pro Gly Ala Glu Thr Thr
65                  70                  75                  80

Ser Asp Val Pro Phe Pro Ser Thr His Leu Leu Met Glu Ala Met Asp
                85                  90                  95

Lys Thr Gln Asn Asp Ile Glu Ile Ile Leu Lys Asp Leu Lys Val Asp
            100                 105                 110

Val Val Phe Tyr Asp Phe Thr His Trp Leu Pro Ser Leu Ala Arg Lys
        115                 120                 125

Ile Gly Ile Lys Ser Val Phe Tyr Ser Thr Ile Ser Pro Leu Met His
    130                 135                 140

Gly Tyr Ala Leu Ser Pro Glu Arg Arg Val Val Gly Lys Gln Leu Thr
145                 150                 155                 160

Glu Ala Asp Met Met Lys Ala Pro Ala Ser Phe Pro Asp Pro Ser Ile
                165                 170                 175

Lys Leu His Ala His Glu Ala Arg Gly Phe Thr Ala Arg Thr Val Met
            180                 185                 190

Lys Phe Gly Gly Asp Ile Thr Phe Phe Asp Arg Ile Phe Thr Ala Val
        195                 200                 205

Ser Glu Ser Asp Gly Leu Ala Tyr Ser Thr Cys Arg Glu Ile Glu Gly
    210                 215                 220

Gln Phe Cys Asp Tyr Ile Glu Thr Gln Phe Gln Lys Pro Val Leu Leu

```
                 225                 230                 235                 240
Ala Gly Pro Ala Leu Pro Val Pro Ser Lys Ser Thr Met Glu Gln Lys
            245                 250                 255

Trp Ser Asp Trp Leu Gly Lys Phe Lys Glu Gly Ser Val Ile Tyr Cys
        260                 265                 270

Ala Phe Gly Ser Glu Cys Thr Leu Arg Lys Asp Lys Phe Gln Glu Leu
    275                 280                 285

Leu Trp Gly Leu Glu Leu Thr Gly Met Pro Phe Phe Ala Ala Leu Lys
290                 295                 300

Pro Pro Phe Glu Thr Glu Ser Val Glu Ala Ile Pro Glu Leu
305                 310                 315                 320

Lys Glu Lys Ile Gln Gly Arg Gly Ile Val His Gly Glu Trp Val Gln
                325                 330                 335

Gln Gln Leu Phe Leu Gln His Pro Ser Val Gly Cys Phe Val Ser His
            340                 345                 350

Cys Gly Trp Ala Ser Leu Ser Glu Ala Leu Val Asn Asp Cys Gln Ile
        355                 360                 365

Val Leu Leu Pro Gln Val Gly Asp Gln Ile Ile Asn Ala Arg Ile Met
    370                 375                 380

Ser Val Ser Leu Lys Val Gly Val Glu Val Lys Gly Glu Glu Asp
385                 390                 395                 400

Gly Val Phe Ser Arg Glu Ser Val Cys Lys Ala Val Lys Ala Val Met
                405                 410                 415

Asp Glu Lys Ser Glu Ile Gly Arg Glu Val Arg Gly Asn His Asp Lys
            420                 425                 430

Leu Arg Gly Phe Leu Met Asn Ala Asp Leu Asp Ser Lys Tyr Met Asp
        435                 440                 445

Ser Phe Asn Gln Lys Leu Gln Asp Leu Leu Gly
    450                 455

<210> SEQ ID NO 14
<211> LENGTH: 1642
<212> TYPE: DNA
<213> ORGANISM: Dianthus caryophyllus cv. light cream candle
<220> FEATURE:
<221> NAME/KEY: CDS
<222> LOCATION: (45)..(1511)

<400> SEQUENCE: 14
cttaaactca tcaatcaata agtaccaaaa gaacaatttc agat atg ggc act gaa      56
                                                Met Gly Thr Glu
                                                  1 cct caa aga cta cat gtt gtg ttc ttc ccg ctt atg gcc gcg ggt cac     104
Pro Gln Arg Leu His Val Val Phe Phe Pro Leu Met Ala Ala Gly His
  5              10                  15                  20 atg atc ccg act tta gac att gca aag cta ttc gcg gca cac cac gtc     152
Met Ile Pro Thr Leu Asp Ile Ala Lys Leu Phe Ala Ala His His Val
             25                  30                  35 aaa acc acc atc gtt acc acc cct tta aac gca ccg act ttt ctc aag     200
Lys Thr Thr Ile Val Thr Thr Pro Leu Asn Ala Pro Thr Phe Leu Lys
         40                  45                  50 cca tta cag tcc tac aca aac atc ggc cct cca atc gat gtc caa gtc     248
Pro Leu Gln Ser Tyr Thr Asn Ile Gly Pro Pro Ile Asp Val Gln Val
     55                  60                  65 att ccg ttc cct gct aag gag gct ggt ctc cct gag gga gtc gag aac     296
Ile Pro Phe Pro Ala Lys Glu Ala Gly Leu Pro Glu Gly Val Glu Asn
 70                  75                  80
```

-continued

| | |
|---|---|
| ttc gag cat ttc aca tca gat gag atg tcg ttg aag ttt ctg aaa gca<br>Phe Glu His Phe Thr Ser Asp Glu Met Ser Leu Lys Phe Leu Lys Ala<br>85                    90                   95                  100 | 344 |
| gcc gag tta cta gaa gaa cct ctt ata caa gta ctt gag agg tgt aac<br>Ala Glu Leu Leu Glu Glu Pro Leu Ile Gln Val Leu Glu Arg Cys Asn<br>                  105                 110                115 | 392 |
| cct aag gct gac tgc tta gtt gct gat atg ctg ctt ccg ttt gcg aca<br>Pro Lys Ala Asp Cys Leu Val Ala Asp Met Leu Leu Pro Phe Ala Thr<br>          120                 125                 130 | 440 |
| gaa gtc gcg gct aag ttt gat att ccg agg ctg gtt ttc cat ggc agt<br>Glu Val Ala Ala Lys Phe Asp Ile Pro Arg Leu Val Phe His Gly Ser<br>               135               140              145 | 488 |
| tgc tgt ttt gcg ctt agt gtc atg gac gct ttc atc aaa tat cag cct<br>Cys Cys Phe Ala Leu Ser Val Met Asp Ala Phe Ile Lys Tyr Gln Pro<br>150                   155                160 | 536 |
| cat aaa gat gtt tcg aac gat gat gaa gaa ttc gtc atc cct cat ctt<br>His Lys Asp Val Ser Asn Asp Asp Glu Glu Phe Val Ile Pro His Leu<br>165                   170               175             180 | 584 |
| ccc cac gag atc aag att acg aga atg caa ttg aat gag ggg gtt aaa<br>Pro His Glu Ile Lys Ile Thr Arg Met Gln Leu Asn Glu Gly Val Lys<br>                  185               190             195 | 632 |
| cag aac aaa caa gac act atg tgg atg gac gtg tta ggc agg gca ctc<br>Gln Asn Lys Gln Asp Thr Met Trp Met Asp Val Leu Gly Arg Ala Leu<br>          200                 205                210 | 680 |
| gag tct gaa att aag agt tat ggt gta att gtt aac agc ttt tac gag<br>Glu Ser Glu Ile Lys Ser Tyr Gly Val Ile Val Asn Ser Phe Tyr Glu<br>               215               220             225 | 728 |
| tta gaa ccc gag tat gct gat ttc tac agg aaa gta atg ggt cgg aaa<br>Leu Glu Pro Glu Tyr Ala Asp Phe Tyr Arg Lys Val Met Gly Arg Lys<br>230                   235                240 | 776 |
| acg tgg caa atc ggt cct gtt tcc ttg tgt aat cga gaa aac gaa gct<br>Thr Trp Gln Ile Gly Pro Val Ser Leu Cys Asn Arg Glu Asn Glu Ala<br>245                   250               255             260 | 824 |
| aag ttt caa aga ggt aaa gac tct tcc att gat gag aac gcg tgc tta<br>Lys Phe Gln Arg Gly Lys Asp Ser Ser Ile Asp Glu Asn Ala Cys Leu<br>               265               270             275 | 872 |
| aaa tgg ctc gac tct aag aag ccg aac tca gtc att tac gta tgc ttt<br>Lys Trp Leu Asp Ser Lys Lys Pro Asn Ser Val Ile Tyr Val Cys Phe<br>280                   285               290 | 920 |
| ggt agc tta acc gaa gtc tca ctg tta caa ctt cac gag atc gca aaa<br>Gly Ser Leu Thr Glu Val Ser Leu Leu Gln Leu His Glu Ile Ala Lys<br>          295                 300                305 | 968 |
| ggg tta gaa gcg tct gag caa aat ttc gta tgg gtg att agg aga agt<br>Gly Leu Glu Ala Ser Glu Gln Asn Phe Val Trp Val Ile Arg Arg Ser<br>310                   315               320 | 1016 |
| aac acg aac ggt gaa gaa aca gaa gat atc ttc cca aaa ggg ttt gaa<br>Asn Thr Asn Gly Glu Glu Thr Glu Asp Ile Phe Pro Lys Gly Phe Glu<br>325                   330               335             340 | 1064 |
| gag cgt acg aaa ggt aag gga cta att ata agg ggt tgg gcc cca caa<br>Glu Arg Thr Lys Gly Lys Gly Leu Ile Ile Arg Gly Trp Ala Pro Gln<br>               345               350             355 | 1112 |
| gta cta att tta gac cac gag gcc gta gga gga ttc gtg aca cac tgt<br>Val Leu Ile Leu Asp His Glu Ala Val Gly Gly Phe Val Thr His Cys<br>360                   365               370 | 1160 |
| gga tgg aac tca act ctg gag ggt atc tcg tgt ggg gta cct atg gtc<br>Gly Trp Asn Ser Thr Leu Glu Gly Ile Ser Cys Gly Val Pro Met Val<br>          375                 380               385 | 1208 |
| act tgg ccc gca ttt gct gag caa ttt tac atc gaa aaa ttg gtg acc<br>Thr Trp Pro Ala Phe Ala Glu Gln Phe Tyr Ile Glu Lys Leu Val Thr<br>390                   395               400 | 1256 |

```
gag att ttg aag acg ggc att cct gtt ggg tcg aaa cat tgg aat aga    1304
Glu Ile Leu Lys Thr Gly Ile Pro Val Gly Ser Lys His Trp Asn Arg
405                 410                 415                 420 acg atc gag tgt aac gta aaa tgg gaa gat ata aag gaa gtt gta aga    1352
Thr Ile Glu Cys Asn Val Lys Trp Glu Asp Ile Lys Glu Val Val Arg
                425                 430                 435 aga tta atg gtt gaa gaa gag ggt atg gag ata aga agt agg gca ttg    1400
Arg Leu Met Val Glu Glu Glu Gly Met Glu Ile Arg Ser Arg Ala Leu
            440                 445                 450 aag tta aag aat atg gca aga aag gct att gat gaa ggt ggt tca tct    1448
Lys Leu Lys Asn Met Ala Arg Lys Ala Ile Asp Glu Gly Gly Ser Ser
        455                 460                 465 tat gtt gaa ttg act tct ttg atc caa gaa tta agc aat tgt aag ctt    1496
Tyr Val Glu Leu Thr Ser Leu Ile Gln Glu Leu Ser Asn Cys Lys Leu
    470                 475                 480 aat agt aat ggt ttt tagtcttctt tccatgaatt gaatgagctt tctatgtctt    1551
Asn Ser Asn Gly Phe
485 tattttttca tcatttacct ttattttatc agatttgtca caagaaattc aagttatttg    1611 gtgtcattat ttcagggcta attttatgaa a                                   1642

<210> SEQ ID NO 15
<211> LENGTH: 489
<212> TYPE: PRT
<213> ORGANISM: Dianthus caryophyllus cv. light cream candle

<400> SEQUENCE: 15

Met Gly Thr Glu Pro Gln Arg Leu His Val Val Phe Pro Leu Met
1               5                   10                  15

Ala Ala Gly His Met Ile Pro Thr Leu Asp Ile Ala Lys Leu Phe Ala
                20                  25                  30

Ala His His Val Lys Thr Thr Ile Val Thr Thr Pro Leu Asn Ala Pro
            35                  40                  45

Thr Phe Leu Lys Pro Leu Gln Ser Tyr Thr Asn Ile Gly Pro Pro Ile
        50                  55                  60

Asp Val Gln Val Ile Pro Phe Pro Ala Lys Glu Ala Gly Leu Pro Glu
65                  70                  75                  80

Gly Val Glu Asn Phe His Phe Thr Ser Asp Glu Met Ser Leu Lys
                85                  90                  95

Phe Leu Lys Ala Ala Glu Leu Leu Glu Glu Pro Leu Ile Gln Val Leu
            100                 105                 110

Glu Arg Cys Asn Pro Lys Ala Asp Cys Leu Val Ala Asp Met Leu Leu
        115                 120                 125

Pro Phe Ala Thr Glu Val Ala Ala Lys Phe Asp Ile Pro Arg Leu Val
    130                 135                 140

Phe His Gly Ser Cys Cys Phe Ala Leu Ser Val Met Asp Ala Phe Ile
145                 150                 155                 160

Lys Tyr Gln Pro His Lys Asp Val Ser Asn Asp Glu Glu Phe Val
                165                 170                 175

Ile Pro His Leu Pro His Glu Ile Lys Ile Thr Arg Met Gln Leu Asn
            180                 185                 190

Glu Gly Val Lys Gln Asn Lys Gln Asp Thr Met Trp Met Asp Val Leu
        195                 200                 205

Gly Arg Ala Leu Glu Ser Glu Ile Lys Ser Tyr Gly Val Ile Val Asn
    210                 215                 220
```

```
Ser Phe Tyr Glu Leu Glu Pro Glu Tyr Ala Asp Phe Tyr Arg Lys Val
225                 230                 235                 240

Met Gly Arg Lys Thr Trp Gln Ile Gly Pro Val Ser Leu Cys Asn Arg
            245                 250                 255

Glu Asn Glu Ala Lys Phe Gln Arg Gly Lys Asp Ser Ser Ile Asp Glu
        260                 265                 270

Asn Ala Cys Leu Lys Trp Leu Asp Ser Lys Lys Pro Asn Ser Val Ile
    275                 280                 285

Tyr Val Cys Phe Gly Ser Leu Thr Glu Val Ser Leu Leu Gln Leu His
290                 295                 300

Glu Ile Ala Lys Gly Leu Glu Ala Ser Glu Gln Asn Phe Val Trp Val
305                 310                 315                 320

Ile Arg Arg Ser Asn Thr Asn Gly Glu Glu Thr Glu Asp Ile Phe Pro
            325                 330                 335

Lys Gly Phe Glu Glu Arg Thr Lys Gly Lys Gly Leu Ile Ile Arg Gly
        340                 345                 350

Trp Ala Pro Gln Val Leu Ile Leu Asp His Glu Ala Val Gly Gly Phe
    355                 360                 365

Val Thr His Cys Gly Trp Asn Ser Thr Leu Glu Gly Ile Ser Cys Gly
370                 375                 380

Val Pro Met Val Thr Trp Pro Ala Phe Ala Glu Gln Phe Tyr Ile Glu
385                 390                 395                 400

Lys Leu Val Thr Glu Ile Leu Lys Thr Gly Ile Pro Val Gly Ser Lys
            405                 410                 415

His Trp Asn Arg Thr Ile Glu Cys Asn Val Lys Trp Glu Asp Ile Lys
        420                 425                 430

Glu Val Val Arg Arg Leu Met Val Glu Glu Gly Met Glu Ile Arg
    435                 440                 445

Ser Arg Ala Leu Lys Leu Lys Asn Met Ala Arg Lys Ala Ile Asp Glu
450                 455                 460

Gly Gly Ser Ser Tyr Val Glu Leu Thr Ser Leu Ile Gln Glu Leu Ser
465                 470                 475                 480

Asn Cys Lys Leu Asn Ser Asn Gly Phe
            485

<210> SEQ ID NO 16
<211> LENGTH: 1993
<212> TYPE: DNA
<213> ORGANISM: Dianthus caryophyllus cv. light cream candle
<220> FEATURE:
<221> NAME/KEY: CDS
<222> LOCATION: (410)..(1852)

<400> SEQUENCE: 16
tccttctgaa tgttgtagtc agcaagagtg cggccgtcct cgagttgctt tccagcgaag      60
atcagacgtt gctggtctgg gggatccct tccttgtcct ggattttggt tttgacattg      120
tcgattgtgt cggaactctc gacctcgaga gtgattgtct tgcctgtgag ggtcttaacg     180
aagatttgca tcttgaaaga aggattaaaa tcgagaggaa gattgattag agaatttgga     240
gagaaaattg attgaattat aagaagttga gaattgagct cgtgccgaat tcggcacgag     300
atcaaacatc aattacacag aaataacaac aacaacaaaa caacaacaac aacaacaaaa     360
caactcttta ttaatccatc aaattaccaa aaaaaaaata tacaggatc atg tct tca     418
                                                        Met Ser Ser
                                                        1 ggg tta gta ttc att cct aca ccg ggt atg ggt cac ctt gta tcc gcc        466
```

```
                Gly Leu Val Phe Ile Pro Thr Pro Gly Met Gly His Leu Val Ser Ala
                  5                  10                  15 atc gag ctc gcc aaa cac gtc ctt cgt acc aat aat ttc atc tcc ata                514
Ile Glu Leu Ala Lys His Val Leu Arg Thr Asn Asn Phe Ile Ser Ile
 20                  25                  30                  35 tcc att ctt att ctc aac att ccg agc cat tcc tcc aaa att acg ggc                562
Ser Ile Leu Ile Leu Asn Ile Pro Ser His Ser Ser Lys Ile Thr Gly
                 40                  45                  50 ttc gtc gac tcc cag tca cgt aac aac cca tac ccg act cgt tta aca                610
Phe Val Asp Ser Gln Ser Arg Asn Asn Pro Tyr Pro Thr Arg Leu Thr
                         55                  60                  65 ttt gtc acc ctc ccg ccc tta tca gac cca cct gac atg gcg ggt acc                658
Phe Val Thr Leu Pro Pro Leu Ser Asp Pro Pro Asp Met Ala Gly Thr
                 70                  75                  80 ccg cac ttc tcg tcg gtc atc cac ctt cac aag ccg atc gtg aag cag                706
Pro His Phe Ser Ser Val Ile His Leu His Lys Pro Ile Val Lys Gln
 85                  90                  95 gcc att gag gac cgt gtt cga gat ggg ttg ttt aaa cct gtc ggg ttt                754
Ala Ile Glu Asp Arg Val Arg Asp Gly Leu Phe Lys Pro Val Gly Phe
100                 105                 110                 115 gtt gtc gac atg ttt tgc gct gaa atg gtt gat ctt gct aat gag atg                802
Val Val Asp Met Phe Cys Ala Glu Met Val Asp Leu Ala Asn Glu Met
                 120                 125                 130 aat gtt ccg acc tac ctt ttc ttt act tcg ggt gca agt ttt ttg aac                850
Asn Val Pro Thr Tyr Leu Phe Phe Thr Ser Gly Ala Ser Phe Leu Asn
                 135                 140                 145 ttc ttg ttg tat gct cag tca ctg gcg gat gat cat ccc gag att gat                898
Phe Leu Leu Tyr Ala Gln Ser Leu Ala Asp Asp His Pro Glu Ile Asp
        150                 155                 160 atc gtg agg gag ttt agt agg cgg gat ttt tct gcg ctt gtg ccc ggg                946
Ile Val Arg Glu Phe Ser Arg Arg Asp Phe Ser Ala Leu Val Pro Gly
        165                 170                 175 ttt cag aac ccg gtc acg agc aat gtt att ccc gct ctc ttg cag gag                994
Phe Gln Asn Pro Val Thr Ser Asn Val Ile Pro Ala Leu Leu Gln Glu
180                 185                 190                 195 aag agc ggg tgt gaa ttg ctc ctc aac ttc gcg agg aag ttt agg gaa                1042
Lys Ser Gly Cys Glu Leu Leu Leu Asn Phe Ala Arg Lys Phe Arg Glu
                200                 205                 210 atg aag ggt att ttg gtg aac acg tat gcg gaa ttg gaa ccg tat ggt                1090
Met Lys Gly Ile Leu Val Asn Thr Tyr Ala Glu Leu Glu Pro Tyr Gly
                215                 220                 225 ctc cag gcg ttg gcc aaa ggt gac ggt aaa aga att ccg ccg gtt tat                1138
Leu Gln Ala Leu Ala Lys Gly Asp Gly Lys Arg Ile Pro Pro Val Tyr
        230                 235                 240 ccc gtg ggg ccc att ttg gag cta cat aaa aag agc ggt cgt ggg acc                1186
Pro Val Gly Pro Ile Leu Glu Leu His Lys Lys Ser Gly Arg Gly Thr
245                 250                 255 acc agt atg gat gag tct gtg att cag tgg ctc gac gct caa ccg gag                1234
Thr Ser Met Asp Glu Ser Val Ile Gln Trp Leu Asp Ala Gln Pro Glu
260                 265                 270                 275 tcg tcg gtg gtg ttt ctg tgt ttt gga agc tgg gga agt ttc gat gag                1282
Ser Ser Val Val Phe Leu Cys Phe Gly Ser Trp Gly Ser Phe Asp Glu
                280                 285                 290 gag cag att aaa gag ata gcc aat ggt cta gaa caa tcg gga cat cgg                1330
Glu Gln Ile Lys Glu Ile Ala Asn Gly Leu Glu Gln Ser Gly His Arg
                295                 300                 305 ttt ttg tgg gcc cta aga aag ccg cct ccc aag gga aag tta gca gca                1378
Phe Leu Trp Ala Leu Arg Lys Pro Pro Pro Lys Gly Lys Leu Ala Ala
        310                 315                 320
```

| | | | | | | | | | | | | | | | |
|---|---|---|---|---|---|---|---|---|---|---|---|---|---|---|---|
| cct | agc | gac | aac | gag | ccg | tac | gta | gag | gcc | ctc | ccg | gaa | ggg | ttc | ctt | 1426 |
| Pro | Ser | Asp | Asn | Glu | Pro | Tyr | Val | Glu | Ala | Leu | Pro | Glu | Gly | Phe | Leu |
| | 325 | | | | 330 | | | | | 335 | | | | | |

| gag | cga | acg | agt | ggt | cgc | ggg | aaa | atc | gta | gcg | tgg | gcc | cca | cag | gtc | 1474 |
| Glu | Arg | Thr | Ser | Gly | Arg | Gly | Lys | Ile | Val | Ala | Trp | Ala | Pro | Gln | Val |
| 340 | | | | | 345 | | | | | 350 | | | | | 355 |

| gag | gtg | tta | gca | cac | cgt | gct | ata | ggt | gga | ttc | gta | tca | cat | tgt | ggg | 1522 |
| Glu | Val | Leu | Ala | His | Arg | Ala | Ile | Gly | Gly | Phe | Val | Ser | His | Cys | Gly |
| | | | | | 360 | | | | | 365 | | | | | 370 |

| tgg | aat | tcc | acg | tta | gag | agt | ttg | tgg | ttt | ggg | gtt | ccc | atg | gca | acg | 1570 |
| Trp | Asn | Ser | Thr | Leu | Glu | Ser | Leu | Trp | Phe | Gly | Val | Pro | Met | Ala | Thr |
| | | | 375 | | | | | 380 | | | | | 385 | | |

| tgg | ccc | atg | tat | gca | gag | caa | cag | atg | aac | gcg | ttt | gag | ctt | gtg | aaa | 1618 |
| Trp | Pro | Met | Tyr | Ala | Glu | Gln | Gln | Met | Asn | Ala | Phe | Glu | Leu | Val | Lys |
| | | 390 | | | | | 395 | | | | | 400 | | | |

| gat | ttg | aat | tta | gca | gtc | gag | ata | aga | atg | gat | tat | aaa | agg | gac | ttg | 1666 |
| Asp | Leu | Asn | Leu | Ala | Val | Glu | Ile | Arg | Met | Asp | Tyr | Lys | Arg | Asp | Leu |
| 405 | | | | | 410 | | | | | 415 | | | | | |

| gta | atg | gga | aaa | agt | aat | ttt | gca | gtg | acc | gcc | gag | gag | att | gaa | aat | 1714 |
| Val | Met | Gly | Lys | Ser | Asn | Phe | Ala | Val | Thr | Ala | Glu | Glu | Ile | Glu | Asn |
| 420 | | | | 425 | | | | | 430 | | | | | 435 | |

| gga | gtt | aaa | aca | ttg | atg | aat | gcg | gat | gga | aag | cta | aga | agt | aga | gta | 1762 |
| Gly | Val | Lys | Thr | Leu | Met | Asn | Ala | Asp | Gly | Lys | Leu | Arg | Ser | Arg | Val |
| | | | 440 | | | | | 445 | | | | | 450 | | |

| acg | aaa | atg | agc | gaa | gaa | ggt | aga | aaa | gct | ttg | gaa | gaa | gga | gga | tcg | 1810 |
| Thr | Lys | Met | Ser | Glu | Glu | Gly | Arg | Lys | Ala | Leu | Glu | Glu | Gly | Gly | Ser |
| | | 455 | | | | | 460 | | | | | 465 | | | |

| tcg | cat | gac | aat | tta | gaa | cat | ttc | att | gaa | gat | gtt | ctt | caa | | | 1852 |
| Ser | His | Asp | Asn | Leu | Glu | His | Phe | Ile | Glu | Asp | Val | Leu | Gln |
| | 470 | | | | 475 | | | | | 480 | | | | taaatcatca tcatttgttg atattttgat aattttttg ttttttagt ctacagtaat    1912 gatgatatta ggttaatgta atcatttta ctacggagta ctcacgtata ttagaatcca    1972 tttaaaaaaa aaaaaaaaa a    1993

<210> SEQ ID NO 17
<211> LENGTH: 481
<212> TYPE: PRT
<213> ORGANISM: Dianthus caryophyllus cv. light cream candle

<400> SEQUENCE: 17

Met Ser Ser Gly Leu Val Phe Ile Pro Thr Pro Gly Met Gly His Leu
1               5                   10                  15

Val Ser Ala Ile Glu Leu Ala Lys His Val Leu Arg Thr Asn Asn Phe
                20                  25                  30

Ile Ser Ile Ser Ile Leu Ile Leu Asn Ile Pro Ser His Ser Ser Lys
            35                  40                  45

Ile Thr Gly Phe Val Asp Ser Gln Ser Arg Asn Asn Pro Tyr Pro Thr
        50                  55                  60

Arg Leu Thr Phe Val Thr Leu Pro Pro Leu Ser Asp Pro Pro Asp Met
65                  70                  75                  80

Ala Gly Thr Pro His Phe Ser Ser Val Ile His Leu His Lys Pro Ile
                85                  90                  95

Val Lys Gln Ala Ile Glu Asp Arg Val Arg Asp Gly Leu Phe Lys Pro
            100                 105                 110

Val Gly Phe Val Val Asp Met Phe Cys Ala Glu Met Val Asp Leu Ala
        115                 120                 125

Asn Glu Met Asn Val Pro Thr Tyr Leu Phe Phe Thr Ser Gly Ala Ser

```
                130             135             140
Phe Leu Asn Phe Leu Leu Tyr Ala Gln Ser Leu Ala Asp Asp His Pro
145                 150                 155                 160

Glu Ile Asp Ile Val Arg Glu Phe Ser Arg Arg Asp Phe Ser Ala Leu
                165                 170                 175

Val Pro Gly Phe Gln Asn Pro Val Thr Ser Asn Val Ile Pro Ala Leu
                180                 185                 190

Leu Gln Glu Lys Ser Gly Cys Glu Leu Leu Asn Phe Ala Arg Lys
            195                 200                 205

Phe Arg Glu Met Lys Gly Ile Leu Val Asn Thr Tyr Ala Glu Leu Glu
210                 215                 220

Pro Tyr Gly Leu Gln Ala Leu Ala Lys Gly Asp Gly Lys Arg Ile Pro
225                 230                 235                 240

Pro Val Tyr Pro Val Gly Pro Ile Leu Glu Leu His Lys Lys Ser Gly
                245                 250                 255

Arg Gly Thr Thr Ser Met Asp Glu Ser Val Ile Gln Trp Leu Asp Ala
                260                 265                 270

Gln Pro Glu Ser Ser Val Val Phe Leu Cys Phe Gly Ser Trp Gly Ser
            275                 280                 285

Phe Asp Glu Glu Gln Ile Lys Glu Ile Ala Asn Gly Leu Glu Gln Ser
290                 295                 300

Gly His Arg Phe Leu Trp Ala Leu Arg Lys Pro Pro Lys Gly Lys
305                 310                 315                 320

Leu Ala Ala Pro Ser Asp Asn Glu Pro Tyr Val Glu Ala Leu Pro Glu
                325                 330                 335

Gly Phe Leu Glu Arg Thr Ser Gly Arg Gly Lys Ile Val Ala Trp Ala
                340                 345                 350

Pro Gln Val Glu Val Leu Ala His Arg Ala Ile Gly Gly Phe Val Ser
                355                 360                 365

His Cys Gly Trp Asn Ser Thr Leu Glu Ser Leu Trp Phe Gly Val Pro
            370                 375                 380

Met Ala Thr Trp Pro Met Tyr Ala Glu Gln Gln Met Asn Ala Phe Glu
385                 390                 395                 400

Leu Val Lys Asp Leu Asn Leu Ala Val Glu Ile Arg Met Asp Tyr Lys
                405                 410                 415

Arg Asp Leu Val Met Gly Lys Ser Asn Phe Ala Val Thr Ala Glu Glu
                420                 425                 430

Ile Glu Asn Gly Val Lys Thr Leu Met Asn Ala Asp Gly Lys Leu Arg
            435                 440                 445

Ser Arg Val Thr Lys Met Ser Glu Glu Gly Arg Lys Ala Leu Glu Glu
450                 455                 460

Gly Gly Ser Ser His Asp Asn Leu Glu His Phe Ile Glu Asp Val Leu
465                 470                 475                 480

Gln

<210> SEQ ID NO 18
<211> LENGTH: 1643
<212> TYPE: DNA
<213> ORGANISM: Dianthus caryophyllus cv. light cream candle
<220> FEATURE:
<221> NAME/KEY: CDS
<222> LOCATION: (68)..(1516)

<400> SEQUENCE: 18
caacactcat aaatttctag taaaacacta aacatttcat aatatatatt attatctaat      60
```

```
ttcggaa atg gtt gcc gag cct cac cgc ctt cac ata gtt atg ttc ccc      109
        Met Val Ala Glu Pro His Arg Leu His Ile Val Met Phe Pro
        1               5                   10 ttc ctg gct cac ggc cac atg att cca aca ctc gac att gcg agg ttg      157
Phe Leu Ala His Gly His Met Ile Pro Thr Leu Asp Ile Ala Arg Leu
15                  20                  25                  30 ttt gca gct cgc aat gtc gaa gtg tcc atc atc acc acc ccg gtc aat      205
Phe Ala Ala Arg Asn Val Glu Val Ser Ile Ile Thr Thr Pro Val Asn
                35                  40                  45 gcg ccg ata ttc acc aag gcc att gaa acg ggt aat ccg ctc atc aat      253
Ala Pro Ile Phe Thr Lys Ala Ile Glu Thr Gly Asn Pro Leu Ile Asn
            50                  55                  60 gtg gag ttg ttc aag ttc ccg gct aaa gaa gcc gga cta ccc gaa ggg      301
Val Glu Leu Phe Lys Phe Pro Ala Lys Glu Ala Gly Leu Pro Glu Gly
        65                  70                  75 tgc gag aat gcc gag ata gta ata agg caa cca gag ttg atc ccg cag      349
Cys Glu Asn Ala Glu Ile Val Ile Arg Gln Pro Glu Leu Ile Pro Gln
80                  85                  90 ttt ttc aag gcc act cac ttg ttc caa cag caa ctc gag gag tac ttg      397
Phe Phe Lys Ala Thr His Leu Phe Gln Gln Gln Leu Glu Glu Tyr Leu
95                  100                 105                 110 gat agg gtt cga ccc gat tgc ctc gtg gcg gat atg ttc tac cca tgg      445
Asp Arg Val Arg Pro Asp Cys Leu Val Ala Asp Met Phe Tyr Pro Trp
                115                 120                 125 gct act gac tcc gcg aca aaa ttt aac cta cct agg ctc gtg ttt cac      493
Ala Thr Asp Ser Ala Thr Lys Phe Asn Leu Pro Arg Leu Val Phe His
            130                 135                 140 ggc att agc tgt ttt gcg cta tgt gcg caa gaa tca gtg tcg cga tat      541
Gly Ile Ser Cys Phe Ala Leu Cys Ala Gln Glu Ser Val Ser Arg Tyr
        145                 150                 155 gaa cct tac cga aac gtc tcg tct gac gac gaa cca ttt gct ctt ccc      589
Glu Pro Tyr Arg Asn Val Ser Ser Asp Asp Glu Pro Phe Ala Leu Pro
160                 165                 170 ggc ctt ccc cat gag ata aag ttg atc cga tcc cag att tcc cca gat      637
Gly Leu Pro His Glu Ile Lys Leu Ile Arg Ser Gln Ile Ser Pro Asp
175                 180                 185                 190 tca aga ggt gac aag gaa aat tca tcc aag acg aca acg gaa ttg atc      685
Ser Arg Gly Asp Lys Glu Asn Ser Ser Lys Thr Thr Thr Glu Leu Ile
                195                 200                 205 aac gat tcc gag gtg gaa agt ttt ggg gtg att atg aac agc ttt tac      733
Asn Asp Ser Glu Val Glu Ser Phe Gly Val Ile Met Asn Ser Phe Tyr
            210                 215                 220 gag ctg gaa cca gaa tat gcc gaa ttt tac gca aag gat atg gga aga      781
Glu Leu Glu Pro Glu Tyr Ala Glu Phe Tyr Ala Lys Asp Met Gly Arg
        225                 230                 235 aag gcg tgg cat atc ggg cca gtt tct ctt tgc aat cga agc aac gac      829
Lys Ala Trp His Ile Gly Pro Val Ser Leu Cys Asn Arg Ser Asn Asp
240                 245                 250 cag aaa gcc cta cga ggg aag cgg gct tca atc gac gac cac gag tgc      877
Gln Lys Ala Leu Arg Gly Lys Arg Ala Ser Ile Asp Asp His Glu Cys
255                 260                 265                 270 ttg gca tgg ctg gac tcg aag gag cct aat tcg gtt gtt tac gtc tgc      925
Leu Ala Trp Leu Asp Ser Lys Glu Pro Asn Ser Val Val Tyr Val Cys
                275                 280                 285 ttc ggg agc aca tcg gtc tcg att gct cca caa ctg cga gaa att gca      973
Phe Gly Ser Thr Ser Val Ser Ile Ala Pro Gln Leu Arg Glu Ile Ala
            290                 295                 300 atg gct cta gaa cag tcc ggt aaa aac ttc att tgg gcg gta cga gat     1021
Met Ala Leu Glu Gln Ser Gly Lys Asn Phe Ile Trp Ala Val Arg Asp
```

```
                 305                 310                 315
ggc gga aat ggg aag aat gag gaa tgg ttg ccg cta gga ttt gag gag    1069
Gly Gly Asn Gly Lys Asn Glu Glu Trp Leu Pro Leu Gly Phe Glu Glu
    320                 325                 330 aga acc aaa ggg aaa ggt cta ata ata cga ggg tgg gcc ccg caa gtc    1117
Arg Thr Lys Gly Lys Gly Leu Ile Ile Arg Gly Trp Ala Pro Gln Val
335                 340                 345                 350 ctt att ttg gac cac aag gcg gtc ggg gct ttt gtg act cac tgt gga    1165
Leu Ile Leu Asp His Lys Ala Val Gly Ala Phe Val Thr His Cys Gly
                355                 360                 365 tgg aac tcg act ctc gaa ggg att tcg gcc ggt gtg ccg atg gtc acg    1213
Trp Asn Ser Thr Leu Glu Gly Ile Ser Ala Gly Val Pro Met Val Thr
            370                 375                 380 tgg ccg ctt ttt gcg gag cag ttc ttc aat gaa aaa cta gtg acc aac    1261
Trp Pro Leu Phe Ala Glu Gln Phe Phe Asn Glu Lys Leu Val Thr Asn
        385                 390                 395 gtt ttg agg acg ggg gtt tcc atc ggg gtt aag aaa tgg aat cga aca    1309
Val Leu Arg Thr Gly Val Ser Ile Gly Val Lys Lys Trp Asn Arg Thr
    400                 405                 410 cct tcg gtc gag gat ctc ata acc cgg gaa gct att gaa gcg gct ata    1357
Pro Ser Val Glu Asp Leu Ile Thr Arg Glu Ala Ile Glu Ala Ala Ile
415                 420                 425                 430 aga gag ata atg gag gga gag aag gca gag gag atg agg ttg aga gca    1405
Arg Glu Ile Met Glu Gly Glu Lys Ala Glu Glu Met Arg Leu Arg Ala
                435                 440                 445 aaa aaa ttg aag gaa gca gcg agg aac gca gta gag gaa ggt ggc tcg    1453
Lys Lys Leu Lys Glu Ala Ala Arg Asn Ala Val Glu Glu Gly Gly Ser
            450                 455                 460 tcg tac aac cac ttg agc act ctg ata gac gag ttg agg aaa tac caa    1501
Ser Tyr Asn His Leu Ser Thr Leu Ile Asp Glu Leu Arg Lys Tyr Gln
        465                 470                 475 act cag aaa cgt aat tagtcctaaa gaattcataa acgctacgca ctatgttttc    1556
Thr Gln Lys Arg Asn
    480 acgctgtcgc atttcattaa ctcttgtgct actgctttaa atttctataa aaggtttgct    1616 gtcgtttaaa aaaaaaaaa aaaaaaa                                        1643

<210> SEQ ID NO 19
<211> LENGTH: 483
<212> TYPE: PRT
<213> ORGANISM: Dianthus caryophyllus cv. light cream candle

<400> SEQUENCE: 19

Met Val Ala Glu Pro His Arg Leu His Ile Val Met Phe Pro Phe Leu
1               5                   10                  15

Ala His Gly His Met Ile Pro Thr Leu Asp Ile Ala Arg Leu Phe Ala
            20                  25                  30

Ala Arg Asn Val Glu Val Ser Ile Ile Thr Thr Pro Val Asn Ala Pro
        35                  40                  45

Ile Phe Thr Lys Ala Ile Glu Thr Gly Asn Pro Leu Ile Asn Val Glu
    50                  55                  60

Leu Phe Lys Phe Pro Ala Lys Glu Ala Gly Leu Pro Glu Gly Cys Glu
65                  70                  75                  80

Asn Ala Glu Ile Val Ile Arg Gln Pro Glu Leu Ile Pro Gln Phe Phe
                85                  90                  95

Lys Ala Thr His Leu Phe Gln Gln Gln Leu Glu Glu Tyr Leu Asp Arg
            100                 105                 110
```

```
Val Arg Pro Asp Cys Leu Val Ala Asp Met Phe Tyr Pro Trp Ala Thr
    115                 120                 125

Asp Ser Ala Thr Lys Phe Asn Leu Pro Arg Leu Val Phe His Gly Ile
130                 135                 140

Ser Cys Phe Ala Leu Cys Ala Gln Glu Ser Val Ser Arg Tyr Glu Pro
145                 150                 155                 160

Tyr Arg Asn Val Ser Ser Asp Asp Glu Pro Phe Ala Leu Pro Gly Leu
                165                 170                 175

Pro His Glu Ile Lys Leu Ile Arg Ser Gln Ile Ser Pro Asp Ser Arg
            180                 185                 190

Gly Asp Lys Glu Asn Ser Ser Lys Thr Thr Glu Leu Ile Asn Asp
        195                 200                 205

Ser Glu Val Glu Ser Phe Gly Val Ile Met Asn Ser Phe Tyr Glu Leu
    210                 215                 220

Glu Pro Glu Tyr Ala Glu Phe Tyr Ala Lys Asp Met Gly Arg Lys Ala
225                 230                 235                 240

Trp His Ile Gly Pro Val Ser Leu Cys Asn Arg Ser Asn Asp Gln Lys
                245                 250                 255

Ala Leu Arg Gly Lys Arg Ala Ser Ile Asp Asp His Glu Cys Leu Ala
            260                 265                 270

Trp Leu Asp Ser Lys Glu Pro Asn Ser Val Val Tyr Val Cys Phe Gly
        275                 280                 285

Ser Thr Ser Val Ser Ile Ala Pro Gln Leu Arg Glu Ile Ala Met Ala
    290                 295                 300

Leu Glu Gln Ser Gly Lys Asn Phe Ile Trp Ala Val Arg Asp Gly Gly
305                 310                 315                 320

Asn Gly Lys Asn Glu Glu Trp Leu Pro Leu Gly Phe Glu Glu Arg Thr
                325                 330                 335

Lys Gly Lys Gly Leu Ile Ile Arg Gly Trp Ala Pro Gln Val Leu Ile
            340                 345                 350

Leu Asp His Lys Ala Val Gly Ala Phe Val Thr His Cys Gly Trp Asn
        355                 360                 365

Ser Thr Leu Glu Gly Ile Ser Ala Gly Val Pro Met Val Thr Trp Pro
    370                 375                 380

Leu Phe Ala Glu Gln Phe Phe Asn Glu Lys Leu Val Thr Asn Val Leu
385                 390                 395                 400

Arg Thr Gly Val Ser Ile Gly Val Lys Lys Trp Asn Arg Thr Pro Ser
                405                 410                 415

Val Glu Asp Leu Ile Thr Arg Glu Ala Ile Glu Ala Ala Ile Arg Glu
            420                 425                 430

Ile Met Glu Gly Glu Lys Ala Gly Glu Met Arg Leu Arg Ala Lys Lys
        435                 440                 445

Leu Lys Glu Ala Ala Arg Asn Ala Val Glu Glu Gly Gly Ser Ser Tyr
    450                 455                 460

Asn His Leu Ser Thr Leu Ile Asp Glu Leu Arg Lys Tyr Gln Thr Gln
465                 470                 475                 480

Lys Arg Asn

<210> SEQ ID NO 20
<211> LENGTH: 1581
<212> TYPE: DNA
<213> ORGANISM: Dianthus caryophyllus cv. light cream candle
<220> FEATURE:
<221> NAME/KEY: CDS
<222> LOCATION: (20)..(1477)
```

<400> SEQUENCE: 20

```
acattacctt taccagaaa atg ggt gct gaa cct aaa cgt cta cac ata gtt      52
                     Met Gly Ala Glu Pro Lys Arg Leu His Ile Val
                      1               5                  10 ttc ttc cct ttt ttg gct cat ggc cat atg att ccg acc ctc gac gtt     100
Phe Phe Pro Phe Leu Ala His Gly His Met Ile Pro Thr Leu Asp Val
             15                  20                  25 gcg agg ctg ttt gca gct cgc aat gtc gag gcg aca ata atc acc acc     148
Ala Arg Leu Phe Ala Ala Arg Asn Val Glu Ala Thr Ile Ile Thr Thr
         30                  35                  40 cgt gtc aac gca cca agg ttt acc agt gca gtt gac acg ggt aac aga     196
Arg Val Asn Ala Pro Arg Phe Thr Ser Ala Val Asp Thr Gly Asn Arg
     45                  50                  55 att gga aat aat caa acg gtc aaa tta gaa ttg tta agg ttc cct acc     244
Ile Gly Asn Asn Gln Thr Val Lys Leu Glu Leu Leu Arg Phe Pro Thr
 60                  65                  70                  75 cac gag gcg ggg gta cct gag ggt tgt gag aat gcg gag att gca atg     292
His Glu Ala Gly Val Pro Glu Gly Cys Glu Asn Ala Glu Ile Ala Met
             80                  85                  90 cgc atc ccg ggg atg atg ccg cga ttt ttt aag ggt acc caa ttg ctt     340
Arg Ile Pro Gly Met Met Pro Arg Phe Phe Lys Gly Thr Gln Leu Leu
         95                 100                 105 cgg gag cag ctc gag cag tac tta agt agg gtt aag ccc aat tgt ctc     388
Arg Glu Gln Leu Glu Gln Tyr Leu Ser Arg Val Lys Pro Asn Cys Leu
    110                 115                 120 gtg gcc gac atg ttt tac ccg tgg gct acg gaa tcc gcg aac aag tat     436
Val Ala Asp Met Phe Tyr Pro Trp Ala Thr Glu Ser Ala Asn Lys Tyr
125                 130                 135 gat atc cct agg ctt gtg ttc cat gga act agc tat ttt tct cta tgc     484
Asp Ile Pro Arg Leu Val Phe His Gly Thr Ser Tyr Phe Ser Leu Cys
140                 145                 150                 155 gca caa gag atc gtt cga gta cac gaa ccg tac aaa atg gtt tta tgt     532
Ala Gln Glu Ile Val Arg Val His Glu Pro Tyr Lys Met Val Leu Cys
            160                 165                 170 aac aac gag aaa ttc act att cct tta att cca cac gac atc aaa ttg     580
Asn Asn Glu Lys Phe Thr Ile Pro Leu Ile Pro His Asp Ile Lys Leu
        175                 180                 185 ttg cga tca caa atg tgc ccg gac tta atc agc gac gag gac aat gac     628
Leu Arg Ser Gln Met Cys Pro Asp Leu Ile Ser Asp Glu Asp Asn Asp
    190                 195                 200 ttt cgt aag cga atg gat ttg gtt aag aag tcg gag gtg gag agt tat     676
Phe Arg Lys Arg Met Asp Leu Val Lys Lys Ser Glu Val Glu Ser Tyr
205                 210                 215 gga gtg att gtg aat agc ttc tac gag ctt gaa ccc gac tat gcc gag     724
Gly Val Ile Val Asn Ser Phe Tyr Glu Leu Glu Pro Asp Tyr Ala Glu
220                 225                 230                 235 gtc tac acg aag gaa ttg gga cga aag gcg tgg cat gta ggg cca gtt     772
Val Tyr Thr Lys Glu Leu Gly Arg Lys Ala Trp His Val Gly Pro Val
            240                 245                 250 tct ctt tgt aat cgt agc gtt ttg gag aag ggt cga aga ggg aat cag     820
Ser Leu Cys Asn Arg Ser Val Leu Glu Lys Gly Arg Arg Gly Asn Gln
        255                 260                 265 gct tca atc gac gag cat gag tgc ttg act tgg ctc gac tcg aag aag     868
Ala Ser Ile Asp Glu His Glu Cys Leu Thr Trp Leu Asp Ser Lys Lys
    270                 275                 280 ctt gct tcc gtt gtt tac att agt ttt ggg agc atg tca tcc tcg atc     916
Leu Ala Ser Val Val Tyr Ile Ser Phe Gly Ser Met Ser Ser Ser Ile
285                 290                 295
```

-continued

| | | |
|---|---|---|
| act cca caa cta cac gag att gcg acg gcc cta gaa aac tcg gga tgt<br>Thr Pro Gln Leu His Glu Ile Ala Thr Ala Leu Glu Asn Ser Gly Cys<br>300                          305                        310                        315 | | 964 |
| aac ttc att tgg gtg gta cga agt ggc gag agt gaa aac cac gac gaa<br>Asn Phe Ile Trp Val Val Arg Ser Gly Glu Ser Glu Asn His Asp Glu<br>                320                        325                        330 | | 1012 |
| agt ttt cca ccg ggg ttc gaa caa agg acc aaa gag aag ggt ttg atc<br>Ser Phe Pro Pro Gly Phe Glu Gln Arg Thr Lys Glu Lys Gly Leu Ile<br>                      335                        340                        345 | | 1060 |
| ata aga ggt tgg gcc cca caa gtc ttg atc ttg gac cac gag gcc gtg<br>Ile Arg Gly Trp Ala Pro Gln Val Leu Ile Leu Asp His Glu Ala Val<br>              350                        355                        360 | | 1108 |
| gga gcg ttc atg aca cac tgt gga tgg aac tcg acg ctg gaa ggg atc<br>Gly Ala Phe Met Thr His Cys Gly Trp Asn Ser Thr Leu Glu Gly Ile<br>365                          370                        375 | | 1156 |
| acg gct ggg gta cca atg atc acg tgg ccg cat gcc gcc gag caa ttc<br>Thr Ala Gly Val Pro Met Ile Thr Trp Pro His Ala Ala Glu Gln Phe<br>380                          385                        390                        395 | | 1204 |
| tac aat gaa aaa cta gtg act gag ata ctg aag agc gga gtg agt gtt<br>Tyr Asn Glu Lys Leu Val Thr Glu Ile Leu Lys Ser Gly Val Ser Val<br>                      400                        405                        410 | | 1252 |
| gga gcg aag ata tgg agt agg atg cct tcg gtc gaa gat ctc ata ggc<br>Gly Ala Lys Ile Trp Ser Arg Met Pro Ser Val Glu Asp Leu Ile Gly<br>                415                        420                        425 | | 1300 |
| cga gag gct att gag att gcg att agg gag gtg atg gac gga gaa aag<br>Arg Glu Ala Ile Glu Ile Ala Ile Arg Glu Val Met Asp Gly Glu Lys<br>              430                        435                        440 | | 1348 |
| gca gaa acg atg agg ttg aag gcg aaa tgg ttg aag gaa atg gcg agg<br>Ala Glu Thr Met Arg Leu Lys Ala Lys Trp Leu Lys Glu Met Ala Arg<br>445                          450                        455 | | 1396 |
| aag gcg gtc gag gaa ggt ggc tcg tcg tac acc cag ttg agt gca ttg<br>Lys Ala Val Glu Glu Gly Gly Ser Ser Tyr Thr Gln Leu Ser Ala Leu<br>460                          465                        470                        475 | | 1444 |
| ata gag gac ttg aag aac tat cac act caa aag tgagattatt aatacatgtt<br>Ile Glu Asp Leu Lys Asn Tyr His Thr Gln Lys<br>                    480                        485 | | 1497 |
| tcaacttcgt tgatctttgt taaaatgtta tgtaatttct tttaataatt cataaagttt | | 1557 |
| aaatgtaaaa aaaaaaaaaa aaaa | | 1581 |

<210> SEQ ID NO 21
<211> LENGTH: 486
<212> TYPE: PRT
<213> ORGANISM: Dianthus caryophyllus cv. light cream candle

<400> SEQUENCE: 21

Met Gly Ala Glu Pro Lys Arg Leu His Ile Val Phe Phe Pro Phe Leu
1               5                  10                 15

Ala His Gly His Met Ile Pro Thr Leu Asp Val Ala Arg Leu Phe Ala
                  20                     25                   30

Ala Arg Asn Val Glu Ala Thr Ile Ile Thr Thr Arg Val Asn Ala Pro
        35                      40                    45

Arg Phe Thr Ser Ala Val Asp Thr Gly Asn Arg Ile Gly Asn Asn Gln
  50                    55                      60

Thr Val Lys Leu Glu Leu Leu Arg Phe Pro Thr His Glu Ala Gly Val
65                    70                     75                    80

Pro Glu Gly Cys Glu Asn Ala Glu Ile Ala Met Arg Ile Pro Gly Met
                  85                     90                   95

Met Pro Arg Phe Phe Lys Gly Thr Gln Leu Leu Arg Glu Gln Leu Glu

```
                100             105             110
Gln Tyr Leu Ser Arg Val Lys Pro Asn Cys Leu Val Ala Asp Met Phe
            115                 120                 125
Tyr Pro Trp Ala Thr Glu Ser Ala Asn Lys Tyr Asp Ile Pro Arg Leu
        130                 135                 140
Val Phe His Gly Thr Ser Tyr Phe Ser Leu Cys Ala Gln Glu Ile Val
145                 150                 155                 160
Arg Val His Glu Pro Tyr Lys Met Val Leu Cys Asn Asn Glu Lys Phe
                165                 170                 175
Thr Ile Pro Leu Ile Pro His Asp Ile Lys Leu Leu Arg Ser Gln Met
            180                 185                 190
Cys Pro Asp Leu Ile Ser Asp Glu Asp Asn Asp Phe Arg Lys Arg Met
        195                 200                 205
Asp Leu Val Lys Lys Ser Glu Val Glu Ser Tyr Gly Val Ile Val Asn
210                 215                 220
Ser Phe Tyr Glu Leu Glu Pro Asp Tyr Ala Glu Val Tyr Thr Lys Glu
225                 230                 235                 240
Leu Gly Arg Lys Ala Trp His Val Gly Pro Val Ser Leu Cys Asn Arg
                245                 250                 255
Ser Val Leu Glu Lys Gly Arg Gly Asn Gln Ala Ser Ile Asp Glu
            260                 265                 270
His Glu Cys Leu Thr Trp Leu Asp Ser Lys Lys Leu Ala Ser Val Val
        275                 280                 285
Tyr Ile Ser Phe Gly Ser Met Ser Ser Ile Thr Pro Gln Leu His
290                 295                 300
Glu Ile Ala Thr Ala Leu Glu Asn Ser Gly Cys Asn Phe Ile Trp Val
305                 310                 315                 320
Val Arg Ser Gly Glu Ser Glu Asn His Asp Glu Ser Phe Pro Pro Gly
                325                 330                 335
Phe Glu Gln Arg Thr Lys Glu Lys Gly Leu Ile Ile Arg Gly Trp Ala
            340                 345                 350
Pro Gln Val Leu Ile Leu Asp His Glu Ala Val Gly Ala Phe Met Thr
        355                 360                 365
His Cys Gly Trp Asn Ser Thr Leu Glu Gly Ile Thr Ala Gly Val Pro
370                 375                 380
Met Ile Thr Trp Pro His Ala Ala Glu Gln Phe Tyr Asn Glu Lys Leu
385                 390                 395                 400
Val Thr Glu Ile Leu Lys Ser Gly Val Ser Val Gly Ala Lys Ile Trp
                405                 410                 415
Ser Arg Met Pro Ser Val Glu Asp Leu Ile Gly Arg Glu Ala Ile Glu
            420                 425                 430
Ile Ala Ile Arg Glu Val Met Asp Gly Glu Lys Ala Glu Thr Met Arg
        435                 440                 445
Leu Lys Ala Lys Trp Leu Lys Glu Met Ala Arg Lys Ala Val Glu Glu
450                 455                 460
Gly Gly Ser Ser Tyr Thr Gln Leu Ser Ala Leu Ile Glu Asp Leu Lys
465                 470                 475                 480
Asn Tyr His Thr Gln Lys
                485

<210> SEQ ID NO 22
<211> LENGTH: 22
<212> TYPE: DNA
<213> ORGANISM: Artificial
```

```
<220> FEATURE:
<223> OTHER INFORMATION: T170F PCR primer

<400> SEQUENCE: 22
gagcaaagca ccgttcgagt tg                                              22

<210> SEQ ID NO 23
<211> LENGTH: 24
<212> TYPE: DNA
<213> ORGANISM: Artificial
<220> FEATURE:
<223> OTHER INFORMATION: T170R PCR Primer

<400> SEQUENCE: 23
ctccgtacat gattgcagag agca                                            24

<210> SEQ ID NO 24
<211> LENGTH: 24
<212> TYPE: DNA
<213> ORGANISM: Artificial
<220> FEATURE:
<223> OTHER INFORMATION: CHIF1 PCR Primer

<400> SEQUENCE: 24
gcaaaaatgt ctcctccagt gtcc                                            24

<210> SEQ ID NO 25
<211> LENGTH: 22
<212> TYPE: DNA
<213> ORGANISM: Artificial
<220> FEATURE:
<223> OTHER INFORMATION: CHIR1 PCR Primer

<400> SEQUENCE: 25
acttctcaat ggcacgaccc tc                                              22

<210> SEQ ID NO 26
<211> LENGTH: 20
<212> TYPE: DNA
<213> ORGANISM: Artificial
<220> FEATURE:
<223> OTHER INFORMATION: T128-NcoI PCR primer

<400> SEQUENCE: 26
acaatttcag ccatgggcac                                                 20

<210> SEQ ID NO 27
<211> LENGTH: 20
<212> TYPE: DNA
<213> ORGANISM: Artificial
<220> FEATURE:
<223> OTHER INFORMATION: A93-75 BspHI PCR primer

<400> SEQUENCE: 27
acaggatcat gacttcaggg                                                 20

<210> SEQ ID NO 28
<211> LENGTH: 24
<212> TYPE: DNA
<213> ORGANISM: Artificial
<220> FEATURE:
<223> OTHER INFORMATION: A93-75-BglII PCR primer

<400> SEQUENCE: 28
ggaagatcta atatacgtga gtac                                            24
```

<210> SEQ ID NO 29
<211> LENGTH: 23
<212> TYPE: DNA
<213> ORGANISM: Artificial
<220> FEATURE:
<223> OTHER INFORMATION: S6B11-RT-F PCR primer

<400> SEQUENCE: 29
gtaatccgct catcaatgtg gag                                          23

<210> SEQ ID NO 30
<211> LENGTH: 22
<212> TYPE: DNA
<213> ORGANISM: Artificial
<220> FEATURE:
<223> OTHER INFORMATION: S6B11-RT-R PCR primer

<400> SEQUENCE: 30
agcaaatggt tcgtcgtcag ac                                           22

<210> SEQ ID NO 31
<211> LENGTH: 18
<212> TYPE: DNA
<213> ORGANISM: Artificial
<220> FEATURE:
<223> OTHER INFORMATION: S12A2-NcoI PCR primer

<400> SEQUENCE: 31
accagaccat gggtgctg                                                18

<210> SEQ ID NO 32
<211> LENGTH: 19
<212> TYPE: DNA
<213> ORGANISM: Artificial
<220> FEATURE:
<223> OTHER INFORMATION: S12A2-S1 PCR primer

<400> SEQUENCE: 32
gagattgcaa tgcgcatcc                                               19

<210> SEQ ID NO 33
<211> LENGTH: 20
<212> TYPE: DNA
<213> ORGANISM: Artificial
<220> FEATURE:
<223> OTHER INFORMATION: S12A2-S2 PCR primer

<400> SEQUENCE: 33
gtggccgaca tgttttaccc                                              20

<210> SEQ ID NO 34
<211> LENGTH: 20
<212> TYPE: DNA
<213> ORGANISM: Artificial
<220> FEATURE:
<223> OTHER INFORMATION: S12A2-A1 PCR primer

<400> SEQUENCE: 34
gcattctcac aaccctcagg                                              20

<210> SEQ ID NO 35
<211> LENGTH: 21
<212> TYPE: DNA
<213> ORGANISM: Artificial
<220> FEATURE:
<223> OTHER INFORMATION: S12A2-A2 PCR primer

<400> SEQUENCE: 35
tctgttaccc gtgtcaactg c                                              21

<210> SEQ ID NO 36
<211> LENGTH: 26
<212> TYPE: DNA
<213> ORGANISM: Artificial
<220> FEATURE:
<223> OTHER INFORMATION: pQE61-f primer

<400> SEQUENCE: 36
catgggaggt accactagtg atatca                                         26

<210> SEQ ID NO 37
<211> LENGTH: 26
<212> TYPE: DNA
<213> ORGANISM: Artificial
<220> FEATURE:
<223> OTHER INFORMATION: pQE61-r primer

<400> SEQUENCE: 37
gatctgatat cactagtggt acctcc                                         26

<210> SEQ ID NO 38
<211> LENGTH: 24
<212> TYPE: DNA
<213> ORGANISM: Artificial
<220> FEATURE:
<223> OTHER INFORMATION: T128-F PCR Primer

<400> SEQUENCE: 38
acgagttaga acccgagtat gctg                                           24

<210> SEQ ID NO 39
<211> LENGTH: 24
<212> TYPE: DNA
<213> ORGANISM: Artificial
<220> FEATURE:
<223> OTHER INFORMATION: T128-R PCR Primer

<400> SEQUENCE: 39
cagtgtgtca cgaatcctcc tacg                                           24

<210> SEQ ID NO 40
<211> LENGTH: 26
<212> TYPE: DNA
<213> ORGANISM: Artificial
<220> FEATURE:
<223> OTHER INFORMATION: PhF3H-ClaI PCR Primer

<400> SEQUENCE: 40
tggttcctgg atcagtgtgt cttttc                                         26

<210> SEQ ID NO 41
<211> LENGTH: 22
<212> TYPE: DNA
<213> ORGANISM: Artificial
<220> FEATURE:
<223> OTHER INFORMATION: ThF3H-SalI1 PCR Primer

<400> SEQUENCE: 41
ttctctgtcg acgcccattg cc                                             22

<210> SEQ ID NO 42

```
<211> LENGTH: 22
<212> TYPE: DNA
<213> ORGANISM: Artificial
<220> FEATURE:
<223> OTHER INFORMATION: ThF3H-SalI2 PCR Primer

<400> SEQUENCE: 42
cgccgtgtcg actcgcttga ag                                              22

<210> SEQ ID NO 43
<211> LENGTH: 20
<212> TYPE: DNA
<213> ORGANISM: Artificial
<220> FEATURE:
<223> OTHER INFORMATION: TpCHI-SalI PCR Primer

<400> SEQUENCE: 43
acgcagaaaa aagtcgactg                                                 20

<210> SEQ ID NO 44
<211> LENGTH: 19
<212> TYPE: DNA
<213> ORGANISM: Artificial
<220> FEATURE:
<223> OTHER INFORMATION: TpCHI-XbaI1 PCR Primer

<400> SEQUENCE: 44
gaggtgattg ggtctagag                                                  19

<210> SEQ ID NO 45
<211> LENGTH: 23
<212> TYPE: DNA
<213> ORGANISM: Artificial
<220> FEATURE:
<223> OTHER INFORMATION: TpCHI-XbaI2 PCR Primer

<400> SEQUENCE: 45
atttctagag caggtccgac aat                                             23

<210> SEQ ID NO 46
<211> LENGTH: 24
<212> TYPE: DNA
<213> ORGANISM: Artificial
<220> FEATURE:
<223> OTHER INFORMATION: PacI-FseIF adapter inserted in a vector

<400> SEQUENCE: 46
taactgcact gaggccggcc agat                                            24

<210> SEQ ID NO 47
<211> LENGTH: 24
<212> TYPE: DNA
<213> ORGANISM: Artificial
<220> FEATURE:
<223> OTHER INFORMATION: PacI-FseIR adapter inserted in a vector

<400> SEQUENCE: 47
ctggccggcc tcagtgcagt taat                                            24

<210> SEQ ID NO 48
<211> LENGTH: 26
<212> TYPE: DNA
<213> ORGANISM: Artificial
<220> FEATURE:
<223> OTHER INFORMATION: M13RV PCR Primer

<400> SEQUENCE: 48
```

-continued tggttcctgg atcagtgtgt ctttc                                              26

<210> SEQ ID NO 49
<211> LENGTH: 33
<212> TYPE: DNA
<213> ORGANISM: Artificial
<220> FEATURE:
<223> OTHER INFORMATION: BamHI-CHI-F PCR Primer

<400> SEQUENCE: 49
tttggatcct ttatattcat gtaatcttag aac                                     33

<210> SEQ ID NO 50
<211> LENGTH: 32
<212> TYPE: DNA
<213> ORGANISM: Artificial
<220> FEATURE:
<223> OTHER INFORMATION: Sal-CHI-R PCR Primer

<400> SEQUENCE: 50
tttgtcgacg tttacaacat caggcccatt tg                                      32

<210> SEQ ID NO 51
<211> LENGTH: 33
<212> TYPE: DNA
<213> ORGANISM: Artificial
<220> FEATURE:
<223> OTHER INFORMATION: Sal-CHI-F PCR Primer

<400> SEQUENCE: 51
tttgtctact ttatattcat gtaatcttag aac                                     33

<210> SEQ ID NO 52
<211> LENGTH: 32
<212> TYPE: DNA
<213> ORGANISM: Artificial
<220> FEATURE:
<223> OTHER INFORMATION: EcoRI-CHI-R PCR Primer

<400> SEQUENCE: 52
tttgaattct attgattcca gcactgcttc ag                                      32

<210> SEQ ID NO 53
<211> LENGTH: 29
<212> TYPE: DNA
<213> ORGANISM: Artificial
<220> FEATURE:
<223> OTHER INFORMATION: YCy3-12P1 PCR Primer

<400> SEQUENCE: 53
ccccatggag agggcagagc tagccttca                                          29

<210> SEQ ID NO 54
<211> LENGTH: 30
<212> TYPE: DNA
<213> ORGANISM: Artificial
<220> FEATURE:
<223> OTHER INFORMATION: YCy3-12P2 PCR Primer

<400> SEQUENCE: 54
aaagcttcac gaagagcgat tgagtacttc                                         30

<210> SEQ ID NO 55
<211> LENGTH: 1670
<212> TYPE: DNA

-continued

```
<213> ORGANISM: Cyclamen persicum
<220> FEATURE:
<221> NAME/KEY: CDS
<222> LOCATION: (62)..(1510)

<400> SEQUENCE: 55
cgactggagc acgaggacac tgacatggac tgaaggaggt agaaaagaac caaagagaaa      60 a atg gag agg gca gag cta gcc ttc atc ccg atc ccg ggt gcc ggc cac    109
  Met Glu Arg Ala Glu Leu Ala Phe Ile Pro Ile Pro Gly Ala Gly His
  1               5                  10                  15 ctc gtg ccc atg gtc gaa ctc gca aaa gcc ctc act aca cga gac gaa    157
Leu Val Pro Met Val Glu Leu Ala Lys Ala Leu Thr Thr Arg Asp Glu
            20                  25                  30 cgc atc tcg gtg aca gtc ttc atc atg gaa gtt cct ttc cag tcc aag    205
Arg Ile Ser Val Thr Val Phe Ile Met Glu Val Pro Phe Gln Ser Lys
        35                  40                  45 ctc aac tcc tac aca caa tcc tta cta tcc aac ccg ccc ccg tct cgt    253
Leu Asn Ser Tyr Thr Gln Ser Leu Leu Ser Asn Pro Pro Pro Ser Arg
    50                  55                  60 gtg cgg ttc gtc cac ctc acc ctg gac gag ccc acg acg gaa gac atc    301
Val Arg Phe Val His Leu Thr Leu Asp Glu Pro Thr Thr Glu Asp Ile
65                  70                  75                  80 cgc tcc aag ccg ggc agc ttc tgg ctg ctc gac tta atc cag att aac    349
Arg Ser Lys Pro Gly Ser Phe Trp Leu Leu Asp Leu Ile Gln Ile Asn
                85                  90                  95 aag tcc cgt gtc aag gac ttt tac tcc tcg gat tca act cgc tac gag    397
Lys Ser Arg Val Lys Asp Phe Tyr Ser Ser Asp Ser Thr Arg Tyr Glu
            100                 105                 110 ctt gct gcc ttc gtg gta gac atg ttc tgt agc cag ttt gcc gag gtg    445
Leu Ala Ala Phe Val Val Asp Met Phe Cys Ser Gln Phe Ala Glu Val
        115                 120                 125 gct agt gaa ttc ggg gtg cca gat tac gtt ttc ttc acc tcg aat gct    493
Ala Ser Glu Phe Gly Val Pro Asp Tyr Val Phe Phe Thr Ser Asn Ala
    130                 135                 140 tat ttc ctc agc ctc atg ttt tat ctt cag gcc att caa gat tac cag    541
Tyr Phe Leu Ser Leu Met Phe Tyr Leu Gln Ala Ile Gln Asp Tyr Gln
145                 150                 155                 160 aat cgg gat atc gcc gag ttc aag gac tcg gac gtc gag ttg tcc att    589
Asn Arg Asp Ile Ala Glu Phe Lys Asp Ser Asp Val Glu Leu Ser Ile
                165                 170                 175 cct ggt ttc atg aac ccg gtc ccc act aag gtc tta cca cac gtt gcg    637
Pro Gly Phe Met Asn Pro Val Pro Thr Lys Val Leu Pro His Val Ala
            180                 185                 190 ttc gac aaa gaa aaa ggc ggg gct ctt ttt ttc gtc gat gtt cca aga    685
Phe Asp Lys Glu Lys Gly Gly Ala Leu Phe Phe Val Asp Val Pro Arg
        195                 200                 205 aag ttg aga aaa acc aag ggg atc ttg gca aat acc ttt gag gag ttt    733
Lys Leu Arg Lys Thr Lys Gly Ile Leu Ala Asn Thr Phe Glu Glu Phe
    210                 215                 220 gaa tcc tac acg att aag tgc ctc gct gag gat gac aag gta ccg cca    781
Glu Ser Tyr Thr Ile Lys Cys Leu Ala Glu Asp Asp Lys Val Pro Pro
225                 230                 235                 240 atc tac aca atc ggg ccc gtc ctc aac ctc aag gcc gaa act agt aat    829
Ile Tyr Thr Ile Gly Pro Val Leu Asn Leu Lys Ala Glu Thr Ser Asn
                245                 250                 255 gac caa aaa gac ctc gtc cag tac gag gaa atc atg gcg tgg ttg gac    877
Asp Gln Lys Asp Leu Val Gln Tyr Glu Glu Ile Met Ala Trp Leu Asp
            260                 265                 270 tgc cag cct tca aca tcc gtg gtg ttt cta tgt ttc ggt agc atg gga    925
Cys Gln Pro Ser Thr Ser Val Val Phe Leu Cys Phe Gly Ser Met Gly
        275                 280                 285
```

|  |  |  |  |  |  |  |  |  | | |  |  |  |  |  | |
|---|---|---|---|---|---|---|---|---|---|---|---|---|---|---|---|---|

```
                      275                 280                 285
acg ttt gag gcg gag cag gtg gtg gaa ata gct act gct ctg gag cat         973
Thr Phe Glu Ala Glu Gln Val Val Glu Ile Ala Thr Ala Leu Glu His
        290                 295                 300 agc gga cac cgg ttc ctg tgg tcc ctt cgg agg cct ccg ccg gag ggc        1021
Ser Gly His Arg Phe Leu Trp Ser Leu Arg Arg Pro Pro Pro Glu Gly
305                 310                 315                 320 aaa aag gaa cct cca tcg gat tac gag aat tta agc gac gtg ctg cca        1069
Lys Lys Glu Pro Pro Ser Asp Tyr Glu Asn Leu Ser Asp Val Leu Pro
                325                 330                 335 gag ggg ttc ctc gat agg acg aaa gag gtt gga aaa gtg ata gga tgg        1117
Glu Gly Phe Leu Asp Arg Thr Lys Glu Val Gly Lys Val Ile Gly Trp
            340                 345                 350 gca ccg cag aca gcg gtg cta tcg cat cct gca gtg gga ggg ttc atc        1165
Ala Pro Gln Thr Ala Val Leu Ser His Pro Ala Val Gly Gly Phe Ile
        355                 360                 365 tcc cac tgc gga tgg aac tct att atg gag agc ttg tgg ttt gga gtg        1213
Ser His Cys Gly Trp Asn Ser Ile Met Glu Ser Leu Trp Phe Gly Val
370                 375                 380 ccc att gct acg tgg ccg tta tac gcg gag caa caa atc aat gcc ttt        1261
Pro Ile Ala Thr Trp Pro Leu Tyr Ala Glu Gln Gln Ile Asn Ala Phe
385                 390                 395                 400 gag atg gtt aag gaa ttg cag ctt gcg gtc gag atc agt ctg gac tat        1309
Glu Met Val Lys Glu Leu Gln Leu Ala Val Glu Ile Ser Leu Asp Tyr
                405                 410                 415 aaa aag gaa aat cat gca ata ctg act gcg gag gag atc gag aga ggg        1357
Lys Lys Glu Asn His Ala Ile Leu Thr Ala Glu Glu Ile Glu Arg Gly
            420                 425                 430 ata aaa cag cta atg gac ggc aac gag agt gtg gaa ata aaa aag aaa        1405
Ile Lys Gln Leu Met Asp Gly Asn Glu Ser Val Glu Ile Lys Lys Lys
        435                 440                 445 gtg aag gca atg agt gag aag agc cgg agt gca gtg gag gag ggc ggg        1453
Val Lys Ala Met Ser Glu Lys Ser Arg Ser Ala Val Glu Glu Gly Gly
450                 455                 460 tct tcg tat gct gcc gtg gga cgc ttc att gag gaa gta ctc aat cgc        1501
Ser Ser Tyr Ala Ala Val Gly Arg Phe Ile Glu Glu Val Leu Asn Arg
465                 470                 475                 480 tct tcg tga aaaacccgg acaagtttca taggactttc atagttatgt                 1550
Ser Ser gaaattttaa tagctcggaa attgcaacat ttgagaaaat gattatgtta aactttgtat      1610
taccagttgc ttttattac atcatctttg cttttagga attaaaaaaa aaaaaaaaa         1670

<210> SEQ ID NO 56
<211> LENGTH: 482
<212> TYPE: PRT
<213> ORGANISM: Cyclamen persicum

<400> SEQUENCE: 56

Met Glu Arg Ala Glu Leu Ala Phe Ile Pro Ile Pro Gly Ala Gly His
1               5                   10                  15

Leu Val Pro Met Val Glu Leu Ala Lys Ala Leu Thr Thr Arg Asp Glu
            20                  25                  30

Arg Ile Ser Val Thr Val Phe Ile Met Glu Val Pro Phe Gln Ser Lys
        35                  40                  45

Leu Asn Ser Tyr Thr Gln Ser Leu Leu Ser Asn Pro Pro Ser Arg
    50                  55                  60

Val Arg Phe Val His Leu Thr Leu Asp Glu Pro Thr Thr Glu Asp Ile
65                  70                  75                  80
```

-continued

```
Arg Ser Lys Pro Gly Ser Phe Trp Leu Leu Asp Leu Ile Gln Ile Asn
                85                  90                  95

Lys Ser Arg Val Lys Asp Phe Tyr Ser Ser Asp Ser Thr Arg Tyr Glu
            100                 105                 110

Leu Ala Ala Phe Val Val Asp Met Phe Cys Ser Gln Phe Ala Glu Val
        115                 120                 125

Ala Ser Glu Phe Gly Val Pro Asp Tyr Val Phe Phe Thr Ser Asn Ala
    130                 135                 140

Tyr Phe Leu Ser Leu Met Phe Tyr Leu Gln Ala Ile Gln Asp Tyr Gln
145                 150                 155                 160

Asn Arg Asp Ile Ala Glu Phe Lys Asp Ser Asp Val Glu Leu Ser Ile
                165                 170                 175

Pro Gly Phe Met Asn Pro Val Pro Thr Lys Val Leu Pro His Val Ala
            180                 185                 190

Phe Asp Lys Glu Lys Gly Gly Ala Leu Phe Phe Val Asp Val Pro Arg
        195                 200                 205

Lys Leu Arg Lys Thr Lys Gly Ile Leu Ala Asn Thr Phe Glu Glu Phe
    210                 215                 220

Glu Ser Tyr Thr Ile Lys Cys Leu Ala Glu Asp Asp Lys Val Pro Pro
225                 230                 235                 240

Ile Tyr Thr Ile Gly Pro Val Leu Asn Leu Lys Ala Glu Thr Ser Asn
                245                 250                 255

Asp Gln Lys Asp Leu Val Gln Tyr Glu Glu Ile Met Ala Trp Leu Asp
            260                 265                 270

Cys Gln Pro Ser Thr Ser Val Val Phe Leu Cys Phe Gly Ser Met Gly
        275                 280                 285

Thr Phe Glu Ala Glu Gln Val Val Glu Ile Ala Thr Ala Leu Glu His
    290                 295                 300

Ser Gly His Arg Phe Leu Trp Ser Leu Arg Arg Pro Pro Pro Glu Gly
305                 310                 315                 320

Lys Lys Glu Pro Pro Ser Asp Tyr Glu Asn Leu Ser Asp Val Leu Pro
                325                 330                 335

Glu Gly Phe Leu Asp Arg Thr Lys Glu Val Gly Lys Val Ile Gly Trp
            340                 345                 350

Ala Pro Gln Thr Ala Val Leu Ser His Pro Ala Val Gly Gly Phe Ile
        355                 360                 365

Ser His Cys Gly Trp Asn Ser Ile Met Glu Ser Leu Trp Phe Gly Val
    370                 375                 380

Pro Ile Ala Thr Trp Pro Leu Tyr Ala Glu Gln Gln Ile Asn Ala Phe
385                 390                 395                 400

Glu Met Val Lys Glu Leu Gln Leu Ala Val Glu Ile Ser Leu Asp Tyr
                405                 410                 415

Lys Lys Glu Asn His Ala Ile Leu Thr Ala Glu Glu Ile Glu Arg Gly
            420                 425                 430

Ile Lys Gln Leu Met Asp Gly Asn Glu Ser Val Glu Ile Lys Lys Lys
        435                 440                 445

Val Lys Ala Met Ser Glu Lys Ser Arg Ser Ala Val Glu Glu Gly Gly
    450                 455                 460

Ser Ser Tyr Ala Ala Val Gly Arg Phe Ile Glu Glu Val Leu Asn Arg
465                 470                 475                 480

Ser Ser
```

```
<210> SEQ ID NO 57
<211> LENGTH: 21
<212> TYPE: DNA
<213> ORGANISM: Artificial
<220> FEATURE:
<223> OTHER INFORMATION: EcoFseI Primer

<400> SEQUENCE: 57
aattcagtca gtggccggcc a                                              21

<210> SEQ ID NO 58
<211> LENGTH: 21
<212> TYPE: DNA
<213> ORGANISM: Artificial
<220> FEATURE:
<223> OTHER INFORMATION: EcoFseR Primer

<400> SEQUENCE: 58
aatttggccg gccactgact g                                              21

<210> SEQ ID NO 59
<211> LENGTH: 21
<212> TYPE: DNA
<213> ORGANISM: Artificial
<220> FEATURE:
<223> OTHER INFORMATION: HinFseR Primer

<400> SEQUENCE: 59
agctcggccg gccactcact a                                              21

<210> SEQ ID NO 60
<211> LENGTH: 21
<212> TYPE: DNA
<213> ORGANISM: Artificial
<220> FEATURE:
<223> OTHER INFORMATION: HinFse3 Primer

<400> SEQUENCE: 60
agcttagtga gtagccggcc g                                              21
```

GLYCOSYLTRANSFERASE GENE

TECHNICAL FIELD

The present invention relates to a gene of an enzyme having an activity which transfers sugar to chalcones and a plant whose flower color has been converted by taking advantage of the glycosyltransferase. More particularly, the invention relates to a gene of an enzyme having an activity which synthesizes a glycoside at position 2' of the chalcones, preferably a gene of an enzyme having the activity which synthesizes the glycoside at position 2' of the chalcones derived from a carnation or a cyclamen, and the use thereof.

BACKGROUND ART

Flower color is an important character when people appreciate or buy flowers and ornamental plants, and the flowers with various colors have been bred traditionally. It is rather rare that a single kind of species has flowers with all colors, and this is due to the fact that biosynthesis of pigments (flower pigments) expressed as the flower colors is genetically defined. It has been substantially impossible to make the flowers with all colors in the target species by crossing because gene resources available for cross breeding are limited to related interfertile species. Only recently, it has become possible to modify the flower color by taking advantage of the gene recombination technology, obtaining a gene of an enzyme involved in synthesis of the flower pigment, and expressing the gene in other species (e.g., Non-patent Document 1, Non-patent Document 2).

Among the flower colors, an orange, red, purple and blue colors are primarily derived from flavonoid referred to as anthocyanin. A yellow color is often derived from compounds such as carotenoid and betalain other than flavonoid, but the yellow color of some plant species is derived from flavonoid. For example, it is known that a glycoside having sugar at position 2' of 4,2',4',6'-tetrahydroxychalcone (THC) is present in petals of a yellow carnation (e.g., Non-patent Document 3). As chalcones, glycosides of THC, butein, and isoliquitigenin are known. As aglycones of the glycosides, The THC is contained in carnation, morning glory, peony, aster and strawflower, 3,4,2', 4', 6'-pentahydroxychalcone is contained in snapdragon and statice, the butein is contained in cosmos and Jerusalem artichoke, and the butein and isoliquitigenin are contained in dahlia. In limited species such as snapdragon, yellow flower pigment referred to as aurones such as aureusidin and brackteatine is present. An absorption maximum of the aurones is 399 nm to 403 nm whereas the absorption maximum of the chalcones is 365 to 382 nm, and thus color tones of both are different (e.g., see Non-patent Document 4). Generally in plant cells, the chalcones and the aurones are stabilized by becoming sugar-transferred glycosides, migrate to and are accumulated in vacuoles. Biosynthetic pathways of anthocyanin are well studied, and enzymes involved in the biosynthesis of anthocyanin and genes encoding them are known (e.g., see Non-patent Document 5). Enzymes involved in the biosynthesis of the aurone and genes thereof have been reported (e.g., see Non-patent Document 6).

The biosynthetic pathways of the flavonoids are present widely in higher plants and common between the species. The THC is biosynthesized from three molecules of malonyl-CoA and one molecule of coumaroyl-CoA by catalysis of chalcone synthase. As shown in FIG. 1, The THC exhibits pale yellow color, but in the plant, it is rapidly converted to colorless naringenin by chalcone isomerase. The THC is also extremely unstable at pH around a neutral, and is converted to naringenin by spontaneously closing a ring. In order for THC to be present stably in the plant cell, i.e., stably exhibit the yellow color, it is described that it is necessary that glycosyltransfer takes place at position 2' of THC and the THC is transported into the vacuole. Therefore, it has been believed that if a gene of the enzyme which transfers the sugar to the position 2' of the THC can be obtained, flowers with yellow color can be made by expressing this enzyme gene in the plant and accumulating THC glycoside (e.g., see Non-patent Document 7).

However, it has been impossible to measure an activity of the enzyme which catalyzes a reaction to transfer the sugar, e.g., glucose to a hydroxyl group at the position 2' of the chalcones including the THC. Conventionally, the activity of chalcone glycosyltransferase has been measured by labeling UDP-glucose with a radioisotope, performing an enzymatic reaction, subsequently extracting a produced glycoside with ethyl acetate and measuring a radioactivity in an extracted organic layer (e.g., see Non-patent Document 8). However, most glycoside of the THC is moved to an aqueous layer, and thus it is most likely that glucose whose radioactivity has been counted is unreacted free UDP-glucose which has been slightly eluted in the organic layer. Therefore, there has been a problem that the original activity of THC glycosyltransferase can not be measured accurately. Accordingly, the enzyme which catalyzes this glycosyltransfer reaction could not be purified, and thus the gene encoding the glycosyltransferase could not be cloned.

It is known that the petals also become the yellow color when a compound where hydroxyl group at position 2' of THC is methylated is accumulated, but neither enzyme which catalyzes this methylation nor gene thereof are known. 6'-Deoxychalcone is contained in yellow varieties of the dahlia and cosmos. In legume, 6'-deoxychalcone is a precursor of 5-deoxyflavonoid and is biosynthesized by catalysis of chalcone synthase (CHS) and chalcone reductase (CHR). It has been reported that a CHR gene of alfalfa was introduced into petunia and then 6'-deoxychalcones such as butein were synthesized. However, when the CHR gene was introduced into the petunia with white flowers, extremely pale yellow color was observed in flower buds, but bloomed flowers were almost white. Thus, this attempt did not lead to production of industrially useful yellow flowers (e.g., see Non-patent Document 9).

Enzymes which catalyze the glycosyltransfer reaction of various flower pigment compounds including flavonoid to produce the glycosides are referred to as glycosyltransferases. The plants have the glycosyltransferases of various molecular species having specificity depending on kinds of the aglycone and the transferred sugar, and genes encoding them. Glucose transferase usually utilizes UDP-glucose as a glucose donor, and thus the glucose transferase includes a motif to bind to the UDP-glucose in an amino acid sequence thereof (e.g., Non-patent Document 10). It is known that there are 99 kinds of genes for the glycosyltransferases having this motif in *Arabidopsis* whose genomic structure has been already shown entirely (e.g., see Non-patent Document 11). The amino acid sequences and functions in some glycosyltransferases have been elucidated. Genes of an enzyme (UDP-glucose: flavonoid 3-glycosyltransferase) which catalyzes a reaction to transfer the glucose to the hydroxyl group at position 3 of the flavonoid or anthocyanidin have been obtained from maize, gentian and grape (e.g., see Non-patent Document 11). Genes of an enzyme (UDP-glucose: anthocyanin 5-glycosyltransferase) which catalyzes a reaction to transfer the glucose to the hydroxyl group at position 5 of anthocyanin have been obtained from *perilla* and *verbena* (e.g., see Non-patent Document 12).

From analyses of the amino acid sequences of these glucose transferases, it has been know that proteins having the same function which catalyzes the glucose transfer reaction are similar in amino acid sequences even when the plant species are different, i.e., the proteins form a family (e.g., see Non-patent Document 11). That is, it has been reported to obtain the enzymes (ortholog) having the same function as that of the glucose transferase where the amino acid sequence and catalysis of the glucose transfer reaction were demonstrated, from the other plant species. For example, the gene of UDP-glucose: anthocyanin 5-glycosyltransferase in the petunia was cloned using the gene of UDP-glucose: anthocyanin 5-glycosyltransferase in the *perilla* (e.g., see Non-patent Document 13). However, even at a current technical level, numerous trials and errors as well as difficulties are involved in acquisition of the gene of glycosyltransferase whose amino acid sequence or function is unknown. In particular, the flower of *Arabidopsis* is white, and no accumulation of chalcone glycoside having the sugar at position 2' has been reported. Therefore, the gene can not be cloned by taking advantage of information for the glycosyltransferase genes of *Arabidopsis* whose genomic structure has been already determined entirely. Concerning the carnation, it has been reported that when mutation occurs in a chalcone isomerase gene and dihydroflavonol reductase gene, the THC glycoside is accumulated to exhibit the yellow color. In the cyclamen, it is also believed that the THC glycoside is accumulated by mutation of chalcone isomerase. Likewise, as the plants in which the chalcone glycoside having the sugar at position 2' is accumulated, petunia pollen, *Paeonia lactiflora*, strawflower, China aster, cyclamen, evening primrose and periwinkle are known. It is also believed that the gene of the enzyme which transfers the sugar to the position 2' of THC is expressed in numerous plants, particularly the plants which exhibit the yellow flower color.

Non-patent Document 1: Plant Cell Physiol., 39:1119 (1998)
Non-patent Document 2: Curr. Opin. Biotechnol., 12:155 (2001)
Non-patent Document 3: Phytochemistry 5:111 (1996)
Non-patent Document 4: Biohorti I 49-57, Seibundo Shinkosha (1990)
Non-patent Document 5: Comprehensive Natural Products Chemistry, Vol. I (ed., Sankawa) pages 713-748, Elsevier Amsterdam (1999)
Non-patent Document 6: Science 290:1163 (2000)
Non-patent Document 7: Biotechnology of Ornamental Plants (ed., Geneve, Preece and Merkle) pages 259-294, CAB International Wallingford, UK (1997)
Non-patent Document 8: Phytochemistry 17:53-56 (1978)
Non-patent Document 9: Plant J., 13:259 (1998)
Non-patent Document 10: Plant Physiol., 112:446 (2001)
Non-patent Document 11: J. Biol. Chem., 276:4338 (2001)
Non-patent Document 12: J. Biol. Chem., 274:7405 (1999)
Non-patent Document 13: Plant Mol. Biol., 48:401-11 (2002)

DISCLOSURE OF THE INVENTION

The present invention provides an enzyme which catalyzes a reaction to transfer sugar to a hydroxyl group at a position 2' of chalcones and a gene thereof, and preferably an enzyme which catalyzes a reaction to transfer glucose to a hydroxyl group at the position 2' of the chalcones and a gene thereof. Furthermore, the invention provides a plant whose flower color has been modified, preferably changed to yellow color using the glycosyltransferase gene.

As described above, no character of glycosyltransferase on position 2' of chalcone has been known, no enzyme has been purified and no gene thereof has been cloned. Using a probe corresponding to a conservative region of the glycosyltransferase from cDNA library of carnation petals, the present inventors cloned several tens of glycosyltransferase genes having nucleotide sequences corresponding to the conservative regions. Furthermore, the present inventors expressed the glycosyltransferase group in *Escherichia coli*, identified activity to transfer glucose to the position 2' of chalcone, i.e., a glycosyltransferase activity on position 2' of chalcone in an extracted solution of *Escherichia coli*, identified that cloned genes encoded the glycosyltransferase at position 2', and completed the invention.

That is, the present invention is:

(1) A gene encoding a protein comprising an amino acid sequence described in SEQ ID NO:2 or an amino acid sequence having deletion, substitution and/or addition of one or more amino acid residues in the amino acid sequence and having an activity to transfer sugar to position 2' of chalcones.

(2) A gene which hybridizes with DNA comprising a nucleotide sequence complementary to a nucleotide sequence described in SEQ ID NO:1 under a stringent condition and encodes a protein having an activity to transfer sugar to position 2' of chalcones.

(3) A gene encoding a protein comprising an amino acid sequence described in SEQ ID NO:15 or an amino acid sequence having deletion, substitution and/or addition of one or more amino acid residues in the amino acid sequence and having an activity to transfer sugar to position 2' of chalcones.

(4) A gene which hybridizes with DNA comprising a nucleotide sequence complementary to a nucleotide sequence described in SEQ ID NO:14 under a stringent condition and encodes a protein having an activity to transfer sugar to position 2' of chalcones.

(5) A gene encoding a protein comprising an amino acid sequence described in SEQ ID NO:17 or an amino acid sequence having deletion, substitution and/or addition of one or more amino acid residues in the amino acid sequence and having an activity to transfer sugar to position 2' of chalcones.

(6) A gene which hybridizes with DNA comprising a nucleotide sequence complementary to a nucleotide sequence described in SEQ ID NO:16 under a stringent condition and encodes a protein having an activity to transfer sugar to position 2' of chalcones.

(7) A gene encoding a protein comprising an amino acid sequence described in SEQ ID NO:19 or an amino acid sequence having deletion, substitution and/or addition of one or more amino acid residues in the amino acid sequence and having an activity to transfer sugar to position 2' of chalcones.

(8) A gene which hybridizes with DNA comprising a nucleotide sequence complementary to a nucleotide sequence described in SEQ ID NO:18 under a stringent condition and encodes a protein having an activity to transfer sugar to position 2' of chalcones.

(9) A gene encoding a protein comprising an amino acid sequence described in SEQ ID NO:21 or an amino acid sequence having deletion, substitution and/or addition of one or more amino acid residues in the amino acid sequence and having an activity to transfer sugar to position 2' of chalcones.

(10) A gene which hybridizes with DNA comprising a nucleotide sequence complementary to a nucleotide sequence described in SEQ ID NO:20 under a stringent condition and encodes a protein having an activity to transfer sugar to position 2' of chalcones.

(11) A gene encoding a protein comprising an amino acid sequence described in SEQ ID NO:56 or an amino acid sequence having deletion, substitution and/or addition of one or more amino acid residues in the amino acid sequence and having an activity to transfer sugar to position 2' of chalcones.

(12) A gene which hybridizes with DNA comprising a nucleotide sequence complementary to a nucleotide sequence described in SEQ ID NO:55 under a stringent condition and encodes a protein having an activity to transfer sugar to position 2' of chalcones.

(13) A vector comprising the gene according to any one of (1) to (12) above.

(14) A host cell transformed with the vector according to (13) above.

(15) A method for producing a protein characterized by culturing or growing the host cells according to (14) above and collecting the protein having an activity to transfer sugar to position 2' of chalcones from the host cells.

(16) A protein obtained by the method according to (15) above.

(17) A plant into which the gene according to any one of (1) to (12) above has been introduced, a plant which is a progeny of the plant, or tissue of the plant.

(18) A cut flower collected from the plant according to (17) above.

(19) A plant of which flower color has been modified by introducing and expressing the gene according to any one of (1) to (12) above into the plant, and a plant which is a progeny of the plant.

(20) The plant according to (18) above characterized in that a modified flower color is yellow.

According to the present invention, a novel gene and an enzyme are provided, the sugar may be specifically transferred to the hydroxyl group at position 2' of chalcones, and the chalcones may be stabilized. The invention is used suitably for production of the plant whose flower color is modified.

BRIEF DESCRIPTION OF THE DRAWINGS

FIG. 2 is a view showing alignments of amino acid sequences of glycosyltransferases derived from plants. Nucleotide sequences corresponding to the amino acid sequences indicated by arrows were used as primers. The DNA amplified by these were used for probes as GT conservative regions in Example 2. Boxed parts are homologous sequences among various GT. Abbreviations are as follows. MG 3GGT: morning glory 3GGT, GGT7: gentian 3GT, HGT8: verbena 5GT, Sb UFGT: Baikal skullcap GT.

BEST MODE FOR CARRYING OUT THE INVENTION

Figure 1:
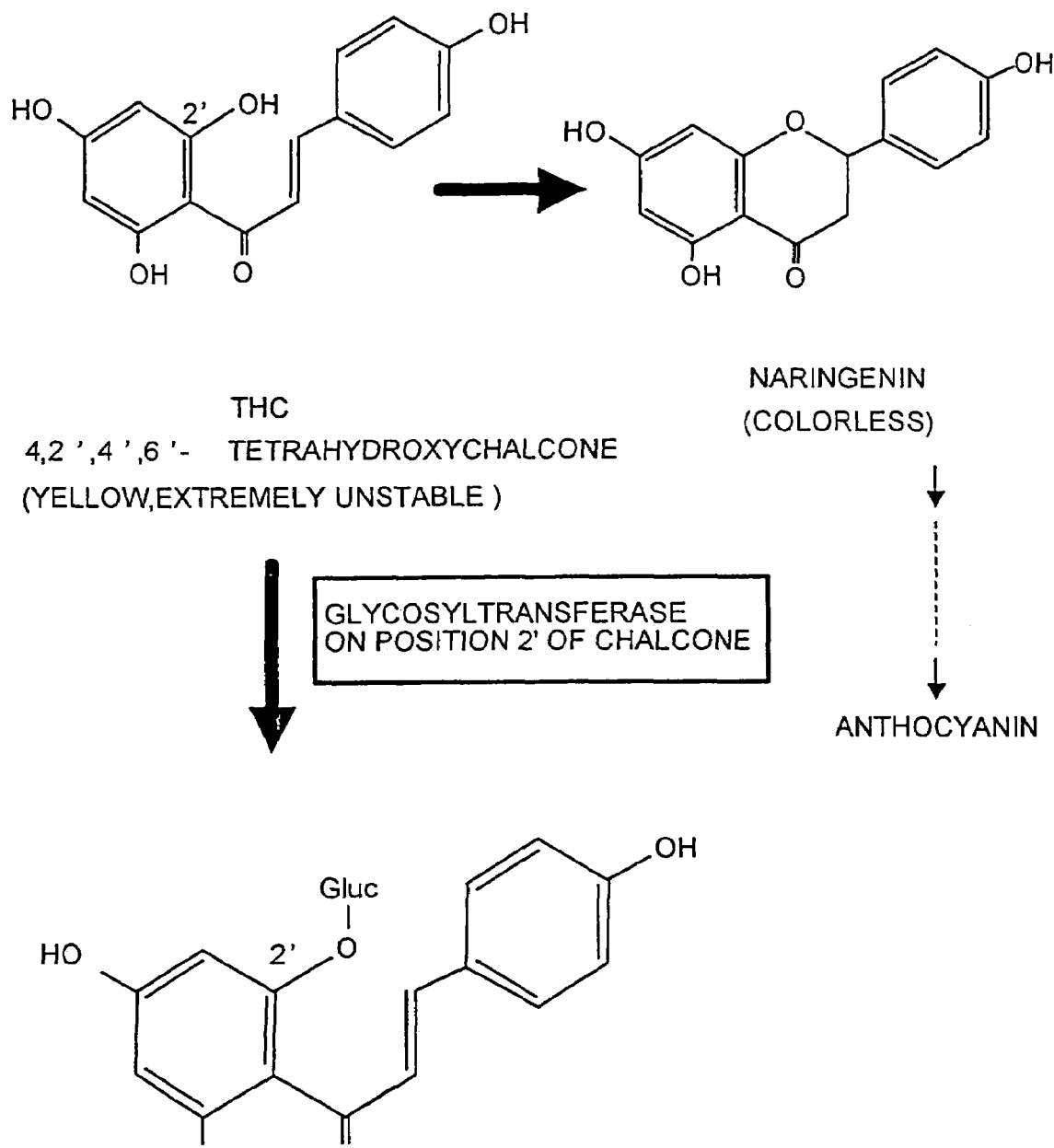
FIG. 1 is a view showing a synthetic pathway of chalcone glycoside at position 2' by glycosyltransferase on position 2' of chalcone.

The gene of the present invention includes one encoding an amino acid sequence described in any of SEQ ID NOS: 2, 15, 17, 19, 21 or 56. However, it has been known that a protein having an amino acid sequence having addition, deletion or substitution of multiple amino acid residues keeps enzymatic activity equivalent to that of the original protein. Therefore, so long as the protein retains glycosyltransferase activity on position 2' of chalcone, the protein having the amino acid sequence with addition, deletion and/or substitution of one or multiple amino acid residues in the amino acid sequence described in SEQ ID NOS: 2, 15, 17, 19, 21 or 56 and the gene encoding the protein belong to the invention. The multiple amino acid residues refer to 2 to 30, preferably 2 to 9 amino acid residues.

The present invention also relates to a gene which hybridizes with DNA having a nucleotide sequence complementary to a nucleotide sequence described in any of SEQ ID NOS: 1, 14, 16, 18, 20 or 55 under a stringent condition and encodes a protein having glycosyltransferase activity on position 2' of chalcone. That is, the gene which hybridizes with DNA having the nucleotide sequence complementary to the nucleotide sequence described in any of SEQ ID NOS: 1, 14, 16, 18, 20 or 55 under a stringent condition and encodes the protein having glycosyltransferase activity at position 2' of chalcone also belongs to the technical scope of the invention. Conditions of hybridization are different depending on lengths of DNA and nucleotide compositions used for a probe, and thus are not limited to concrete conditions shown by numerical values below. As referred to herein, the "stringent condition" is preferably 5×SSC and 37° C., more preferably 5×SSC and 50° C., and still more preferably 2×SSC and 65° C. Herein, the condition of 5×SSC and 37° C. may be applied as the condition where a homolog such as the glycosyltransferase on position 2' of chalcone of the invention is hybridized using a conservative region of the glycosyltransferase gene of anthocyanidins as a probe as shown in Example 2. The condition of 5×SSC and 50° C. may be applied preferably as the condition where the gene (ortholog) of the glycosyltransferase on position 2' of chalcone from other source is hybridized using the gene of the glycosyltransferase on position 2' of chalcone derived from the carnation of the invention as the probe.

The gene selected by the aforementioned hybridization includes naturally occurring substances, e.g., those derived from plants, e.g., those derived from the cyclamen, but is not limited to those derived from the plants. That is, the gene of the glycosyltransferase on position 2' of chalcone of the invention is not limited to the gene of the glycosyltransferase on position 2' of chalcone derived from the carnation, and may be the gene of the glycosyltransferase on position 2' of chalcone derived from the plants such as cyclamen and *Paeonia lactiflora* containing the glycoside having the sugar at position 2' of chalcones, which is a ortholog of the gene. Any of the related genes may be used for breeding yellow flowers. The gene selected by the hybridization may be cDNA or genomic DNA.

The gene having homology to the conservative region in the glycosyltransferase is obtained by screening a cDNA library made from the carnation petals as shown in Example. DNA encoding the glycosyltransferase having the amino acid sequence modified from the amino acid sequence in SEQ ID NO:2 may be synthesized using DNA having the nucleotide sequence described in SEQ ID NO:1 by site-directed mutagenesis and PCR method known publicly. DNA encoding the glycosyltransferase having the amino acid sequence modified from the amino acid sequence in SEQ ID NO:15 may be also synthesized using DNA having the nucleotide sequence described in SEQ ID NO:14 by site-directed mutagenesis and PCR method known publicly. DNA encoding the glycosyltransferase having the amino acid sequence modified from the amino acid sequence in SEQ ID NO:17 may be also synthesized using DNA having the nucleotide sequence described in SEQ ID NO:16 by site-directed mutagenesis and PCR method known publicly. DNA encoding the glycosyltransferase having the amino acid sequence modified from the amino acid sequence in SEQ ID NO:19 may be also synthesized using DNA having the nucleotide sequence described in SEQ ID NO:18 by site-directed mutagenesis and PCR method known publicly. DNA encoding the glycosyltransferase having the amino acid sequence modified from the amino acid sequence in SEQ ID NO:21 may be also synthesized using DNA having the nucleotide sequence described in SEQ ID NO:20 by site-directed mutagenesis and PCR method known publicly. DNA encoding the glycosyltransferase having the amino acid sequence modified from the amino acid sequence in SEQ ID NO:56 may be also synthesized using DNA having the nucleotide sequence described in SEQ ID NO:55 by site-directed mutagenesis and PCR method known publicly. For example, a DNA fragment corresponding to an amino acid sequence to be modified may be obtained by treating cDNA or genomic DNA with restriction enzymes, and using this as a template, the site-directed mutagenesis or the PCR may be performed using primers corresponding to the desired modified amino acid sequence to yield a DNA fragment corresponding to the modified desired amino acid sequence. Subsequently, this DNA fragment in which modification is introduced may be ligated to DNA fragments encoding the other parts of the target enzyme.

Alternatively, to obtain DNA encoding the enzyme composed of a shortened amino acid sequence, DNA encoding a longer amino acid sequence than the target amino acid sequence, e.g., a full length amino acid sequence may be cut with a desired restriction enzyme. When the resulting DNA fragment does not encode the whole target amino acid sequence, a DNA fragment corresponding to an amino acid sequence of lacked parts may be synthesized and ligated.

The resulting glycosyltransferase gene may be identified to encode the protein which exhibits the glycosyltransferase activity on position 2' of chalcone by expressing the glycosyltransferase gene obtained in this way using a gene expression system in *Escherichia coli* or yeast, and measuring the glycosyltransferase activity on position 2' of chalcone in an extracted solution of the *Escherichia coli* or yeast. The glycosyltransferase activity on position 2' of chalcone may be measured by absorbing chalcones which is a substrate of the glycosyltransferase activity on position 2' of chalcone onto a gel filtration resin, subsequently reacting the gel filtration resin with the extracted solution of *Escherichia coli* or yeast transformed with the glycosyltransferase gene and analyzing the produced chalcone glycoside having the sugar at position 2' by high performance liquid chromatography.

Furthermore, a protein of the glycosyltransferase on position 2' of chalcone, which is a product of the gene may be obtained by expressing the gene of glycosyltransferase on position 2' of chalcone in appropriate host cells. Alternatively, using an antibody against the protein or peptide having all or a part of the amino acid sequence described in SEQ ID NO:2, the gene of glycosyltransferase on position 2' of chalcone derived from the other organism may be obtained by expression cloning. For the amino acid sequences of SEQ ID NOS: 15, 17, 19, 21 and 56, the same may be performed.

The present invention also relates to a recombinant vector, particularly an expression vector containing the gene of glycosyltransferase on position 2' of chalcone, and a host cell transformed with the vector. As the host cell, a prokaryotic organism or a eukaryotic organism may be used. The host cells known conventionally and publicly such as bacteria belonging to *Escherichia*, e.g., *Escherichia coli* and bacteria belonging to *Bacillus*, e.g., *Bacillus subtilis* may be used. As eukaryotic cells, eukaryotic microorganisms, preferably yeast and filamentous fungi may be used. The yeast may include *Saccharomyces* yeast such as *Saccharomyces cerevisiae*, and the filamentous fungi may include *Aspergillus* fungi such as *Aspergillus oryzae* and *Aspergillus niger*, and *Penicillium* fungi. Furthermore, animal cells and plant cells may be used as the host cells, and as the animal cells, cell systems of a mouse, hamster, monkey and human are used. Additionally, insect cells, e.g., silk worm cells and an adult silk worm itself are used as the host cells.

The expression vector of the invention contains expression controlling regions such as promoter and terminator, and a replication origin depending on a biological species of the host to which they should be introduced. As the promoter for the bacteria, particularly the promoter of the expression vector in *Escherichia coli*, the promoters known conventionally and publicly, e.g., a trc promoter, a tac promoter, and a lac promoter may be used. As the promoter for the yeast, a glyceraldehyde 3-phosphate dehydrogenase promoter and a PHO5 promoter may be used. As the promoter for the filamentous fungi, promoters of amylase and trp C may be used. However, the promoters are not limited thereto. As the promoter for the animal cells, viral promoters such as SV40 early promoter and SV40 late promoter are used. The expression vector may be made according to standard methods using restriction enzymes and ligase. The host cells may be transformed with the expression vector according to the method known conventionally and publicly.

In construction of the plant expression vector, when using *Agrobacterium*, a binary vector such as pBI121 may be used, and when using a particle gun, an *Escherichia coli* vector such as pUC19 may be used. Furthermore, a plant transformed with the gene of glycosyltransferase on position 2' of chalcone may be obtained by selecting plant cells transformed with the plant expression vector using a marker gene such as antibiotic resistant gene, and redifferentiating using a condition of an appropriate plant hormone and the like. A plant with modified flower color may be obtained by cultivating the transformed plant to bloom.

The objective glycosyltransferase on position 2' of chalcone may be isolated and purified from a culture or a plant by culturing or cultivating the host cells or the transformed plant transformed with the expression vector, and using filtration, centrifugation, disruption of cells, gel filtration chromatography and ion exchange chromatography according to the standard methods.

The present invention is not limited to only the genes of glycosyltransferase on position 2' of chalcone in the carnation and cyclamen. Sources for the gene of glycosyltransferase on position 2' of chalcone may be plants, animals or microorganisms. So long as a protein which the gene encodes has the glycosyltransferase activity at position 2' of chalcone, the gene may be similarly utilized for the conversion of flower colors. The present invention also relates to the use of the gene of glycosyltransferase on position 2' of chalcone. A plant with modified flower color by introducing and expressing the gene of glycosyltransferase on position 2' of chalcone in the plant, or a progeny plant thereof or tissue of these plants is within the technical scope of the invention, and a form of the tissue may be a cut flower.

With the use of a current technical level, it is possible to introduce a gene into a plant and express the gene constitutively or specifically for tissue. It is also possible to inhibit the expression of the target gene by an antisense method and a co-suppression method. Examples of plants capable of being transformed may include, but are not limited to, rose, chrysanthemum, carnation, snapdragon, cyclamen, orchid, *Eustoma russelloanum, freesia*, gerbera, gladiolus, gypsophila, kalanchoe, lily, pelargonium, geranium, petunia, torenia, tulip, rice plant, barley, wheat, rapeseed, potato, tomato, poplar, banana, eucalyptus, sweet potato, soybean, alfalfa, lupine, maize, cauliflower and periwinkle.

As another embodiment of the method for modifying the flower color, means for introducing the gene of glycosyltransferase on position 2' of chalcone of the invention as in the above as well as inhibiting metabolism to convert THC to a substance other than chalcone glycoside having the sugar at position 2' of chalcone may be employed. For example, a form where the gene of glycosyltransferase on position 2' of chalcone of the invention is introduced as well as the expression of one or more genes selected from the gene group of CHI gene (EMBO J., 7:1257, 1988), flavanone 3 hydroxylase gene (F3H) of petunia (Britsh et al., European J. Biochemistry 217:745-754, 1993) and dihydroflavonol 4 reductase gene (DFR) (Beld et al., Plant Molecular Biology 13:491-502, 1989; Huits et al., Plant J., 6:295-310, 1994) is inhibited may be employed.

EXAMPLES

The present invention will be described in detail with reference to the following Examples. Molecular biological techniques were performed according to methods described in WO 96/25500 or Molecular Cloning (Sambrook et al., Cold Spring Harbor Laboratory Press, 1989) unless otherwise indicated.

Example 1

Construction of cDNA Library of Carnation Flower Petal

RNA was isolated from 5 g of fresh flower petals of yellow carnation by a method using guanidine thiocyanate/cesium chloride shown in detail in "Method in Molecular Biology" Vol. 2 (Humana Press Inc., 1984), and poly-A+RNA was purified using Oligotex dT30 (Nippon Roche KK). A cDNA library was constructed from this poly-A+RNA using cDNA synthesis Kit (Stratagene) and λZAPIIUni-XR vector Kit (Stratagene). The resulting library contained $1.6 \times 10^5$ plaque forming units.

Example 2

Isolation of Full Length Gene of Glycosyltransferase on Position 2' of Chalcone

Figure 2:
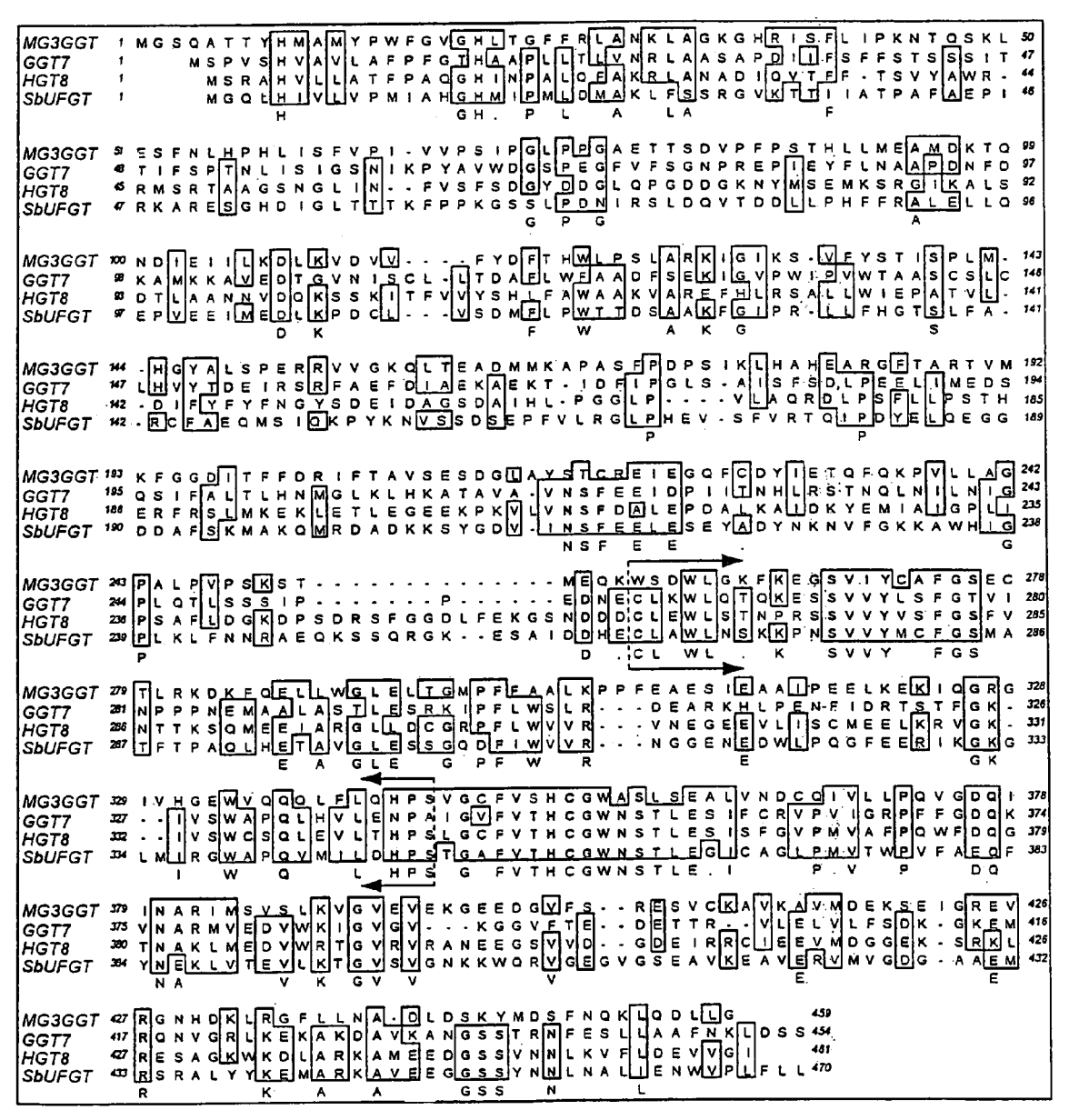

DNA fragments composed of nucleotide sequences corresponding to conservative regions (regions indicated by paired arrows in FIG. 2) obtained by comparing the amino acid sequences of glycosyltransferases (GT) shown in FIG. 2 were amplified, and using them as probes, the cDNA library of the carnation described in Example 1 was screened. The compared amino acid sequences are 4 kinds of the amino acid sequences of UDP glucose: anthocyanidin 3-glycoside glycosyltransferase (3GGT) derived from the morning glory (amino acid sequence described in SEQ ID NO:13), UDP-glucose: anthocyanin 3-glycosyltransferase (3GT) derived from the gentian (Plant Cell Physiol., 37:711, 1996), UDP-glucose: anthocyanin 5-glycosyltransferase (5GT) derived from the verbena (J. Biol. Chem., 274:7405, 1999) and Scutellaria baicalensis glycosyltransferase (GT) (Planta 210: 1006-1013, 2000). For each GT, an oligonucleotide which can amplify the conservative region indicated by arrows with opposed directions was made, and labeled by PCR with DIG labeling system (Roche Diagnostics) according to the condition recommended by the manufacturer. Then, 25 cycles of the reaction composed of 95° C. for 1 min, 55° C. for 1 min and 72° C. for 2 min were performed using the plasmid containing 1 ng of each cDNA as a template, and 100 ng or less of respective oligonucleotides as primers. Using a mixture where equivalent amounts of these PCR products were mixed as a probe of hybridization, the cDNA library derived from the carnation described in Example 1 was screened. The primers used for amplification of the conservative regions are as follows.

Oligonucleotide Sequences

```
Morning glory 3GGT
5'-GAA ATG GTC GGA TTG GCT GGG-3':     SEQ ID NO:3

5'-ACC TCC ACC CCA ACT TTC AGG-3':     SEQ ID NO:4

Gentian 3GT
5'-TGC CTC AAA TGG CTT CAA ACT-3':     SEQ ID NO:5

5'-CCA CCT TTC ACC CCA ACC CC-3':      SEQ ID NO:6

Verbena 5GT
5'-TGC CTC GAA TGG TTG AGC ACG-3':     SEQ ID NO:7

5'-CTC TCA CTC TCA CAC CCG-3':         SEQ ID NO:8

Scutellaria baicalensis GT
5'-CAC GAA TGC TTA GCA TGG CTC-3':     SEQ ID NO:9

5'-CTT ATT GCC CAC TGA AAC CCC-3':     SEQ ID NO:10
```

Screening of the library was performed using a non-radioactive system DNA detection kit (supplied from Roche Diagnostics). The hybridization was performed in 5×SSC containing 1% SDS and 30% formamide at 37° C. overnight. A filter was washed with 1×SSC and 1% SDS at 55° C. for 30 min. About 270 thousands of plaques were screened, and eventually about 30 clones containing the glycosyltransferase gene were obtained. Among these clones, one clone where the glycosyltransferase activity on position 2' of chalcone had been identified by methods described in Examples 4 and 5 was obtained, the clone was designated as T170, and a total nucleotide sequence thereof was determined. The nucleotide sequence was determined by a primer walking method with synthetic oligonucleotide primers using a DNA Sequencer model 3100 (Applied Biosystems). The nucleotide sequence and the amino acid sequence encoded by the nucleotide sequence were shown in SEQ ID NOS:1 and 2, respectively.

Example 3

Amino Acid Sequence Analysis of Glycosyltransferase on Position 2' of Chalcone, T170 pT170 contained the gene T170 of 1709 bp encoding a protein with molecular weight of 54.2 kDa composed of 490 amino acid residues. The amino acid sequence encoded by the T170 gene was compared with those of glycosyltransferases already reported, and consequently, exhibited 25% homology with GT derived from livingstone daisy (Plant J. 19, 509 (1999)) and 21% homology with 5GT derived from perilla and verbena. Software used was Clustal W included in MacVector ver. 6.0 (Oxford Molecule), and the analysis was performed under the condition of matrix blosum: 30, ketuple: 1, gap penalty: 3, topdiagonals: 5, and window size: 5. In BLAST search (the search was performed under the default condition. That is, under the condition of composition-based statistics: on, choose filter: low, complexity matrix: blosum 62, gap costs: existence 11 and extention 1), the homology with those of various GT was observed. For example, the 55% homology with betanidine 6GT derived from the livingstone daisy (Planta, 214:492, 2002), the 45% homology with tobacco GT induced by salicylic acid (Accession Number AB052557, Eur. J. Biochem., 268:4086, 2001), and the 44% homology with tobacco NTGT3 (Accession Number AB072918) were observed in amino acid sequences.

It is known that the enzymes having the same function and activity resemble in amino acid sequences and form a family. In also GT, as shown FIG. 2, 3GGT derived from the morning glory, 3GT derived from the gentian, 5GT derived from the verbena and GT derived from the Scutellaria baicalensis form the family. The amino acid sequence of the glycosyltransferase on position 2' of chalcone of the invention exhibits only the low homology with the amino acid sequences of these 4 kinds of GT, and does not belong to this family. The glycosyltransferase of the invention exhibited the relatively high homology with the betanidine 6GT derived from the livingstone daisy, the tobacco GT induced by salicylic acid and the tobacco NTGT3 described above, but no glycosyltransfer activity on the chalcone has been identified in these GT.

Example 4

Expression of T170 Gene in Escherichia coli

Expression of the T170 gene in Escherichia coli was performed using The QIA expressionist (Qiagen). First, to introduce an Nco I recognition sequence at 5' side of an initiation codon of the glycosyltransferase gene on the T170, a PCR reaction was performed using two primers, T170-NcoI and M13M4 shown below.

```
T170-NcoI:
5'-AGT TCA ACC ATG GGC AAA GCA C-3'   (SEQ ID NO:11)

M13M4:
5'-GTT TTC CCA GTC ACG AC-3'          (SEQ ID NO:12)
```

A PCR reaction mixture (25 µL) is composed of 100 ng of T170, 1× Ex-Taq buffer (Takara), 0.2 mM dNTPs, 0.2 pmol/µL of respective primers and 1.25 U of Ex-Taq polymerase. After reacting at 94° C. for 5 min, 25 cycles of the reaction of 94° C. for 1 min, 55° C. for 1 min and 72° C. for 2 min were performed, and finally the reaction solution was treated at 72° C. for 7 min. The resulting PCR product was subcloned into a pCR2.1 TOPO vector (Invitrogen) according to the method recommended by the manufacturer. A plasmid obtained in this way was designated as the plasmid pTOPO-T170. It was confirmed by sequencing that there was no error in the PCR reaction. pQE60 (Qiagen) was digested with Nco I and Bgl II, and subsequently an oligonucleotide cassette where complementary primers, pQE61-f and pQE61-r had been annealed was inserted in the same site to prepare a vector pQE-61 wherein MCS had been newly introduced.

```
                                        (SEQ ID NO:36)
(pQE61-f) 5'-CATGGGAGGTACCACTAGTGATATCA-3'

(SEQ ID NO:37)
(pQE61-r) 5'-GATCTGATATCACTAGTGGTA CCT CC-3'
```

An about 1.8 kb fragment obtained by treating the plasmid pTOPO-T170 with restriction enzymes, Nco I, Kpn I and Pst I was ligated to sites of the vector pQE-61 cut with Nco I and KpnI to yield a plasmid pSB1443. Competent high JM109 (Toyobo) was transformed with pSB1443.

Example 5

Measurement of Glycosyltransferase Activity of T170 cDNA Recombinant Protein

The transformed Escherichia coli (E. coli) strain obtained in Example 4 was cultured in 3 ml of LB medium containing 50 µg/mL of ampicillin at 37° C. overnight with shaking. Then, 200 µL of the culture was added in 10 mL of an M9 medium containing 50 µg/mL of ampicillin and 0.5% casamino acids, and cultured until A600=0.6 to 1.0 was accomplished. Subsequently, IPTG (isopropyl-β-D-thiogalactopyranoside) was added at a final concentration of 0.02 mM, further the cultivation was continued at 27° C. overnight with shaking, and bacteria were collected by cold centrifugation (3,000 rpm, 10 min, 4° C.). Microbial cells were suspended in 10 mL of buffer (30 mM Tris-HCl, pH 7.5, 30 mM NaCl), E. coli was ultrasonically disrupted, then the centrifugation (15,000 rpm, 10 min, 4° C.) was performed, and the resulting supernatant was used as a crude enzyme solution for the following activity measurement.

THC (500 µg/mL in ethanol) was loaded on gel filtration resin, 1 mL of Toyopearl HW-40F (Tosoh) equilibrated with distilled water with diluting with 3 mL distilled water, and then washed with water. To 100 µL of this resin, 200 µL of the crude enzyme solution and 10 µL of 5 mM of UDP-glucose were added, and reacted at 30° C. for 2 hours. After removing a centrifuged supernatant and washing with water, the reaction was stopped by adding 300 µL of 50% acetonitrile containing 0.1% TFA (trifluoroacetic acid). Flavonoid was separated from the resin by ultrasonic treatment. The solution was centrifuged at 15,000 rpm at 4° C. for 5 min. The resulting supernatant was filtrated with a filter (pore size 0.45 µm, 4 mm, Millex-LH, Millipore) to remove insoluble substances, and then analyzed by high performance liquid chromatography. Analytical conditions of the chalcone and a glycoside thereof are as follows.

YMC-ODS-A312 (6 mmφ×150 mm, K.K. YMC) was used for a column, and $H_2O$ containing 2% acetic acid was used as A solution and methanol was used as B solution in a mobile phase. Elution was performed with linear concentration gradient of 15% to 40% of B solution for 15 min, then kept at 40% of B solution for 5 min, further performed with linear concentration gradient of 40 to 62% of B solution, and subsequently kept at 62% of B solution for 2 min. A flow rate was 1.0 mL/min. Detection was performed by absorbance at 360 nm and absorption spectrum at 250 to 400 nm using a PDA detector, SPD-M6A (Shimadzu Corporation). Using standard preparations of THC and the glycoside having the glucose at position 2' of THC, it was confirmed that the THC and the glycoside having the glucose at position 2' thereof was eluted at retention time of 27.3 min and 19.89 min, respectively.

The extracted solution of E. coli in which the glycosyltransferase gene derived from the T170 had been expressed was reacted, and consequently, a new substance eluted at 19.89 min was detected in addition to THC (retention time: 27.3 min). This is believed to be a product produced by the glycosyltransferase derived from the T170 because no new substance was detected in the reacted crude extracted solution similarly prepared from E. coli in which the pQE-61 vector alone has been expressed.

From the above results, it has been confirmed that the glycosyltransferase derived from the T170 has the activity to transfer the glucose to a hydroxyl group at position 2' of the THC.

Example 6

Construction of Expression Vector of T170 for Plant

In order to demonstrate the function of the gene product of the glycosyltransferase on position 2' of chalcone derived from the T170 in the plant, a binary vector (pSPB1342) was constructed. The vector allowed to express c DNA T170 encoding the protein having the activity to transfer the sugar to the position 2' of THC whereas to inhibit the expression of CHI-A gene (EMBO J., 7:1257, 1988), one of CHI genes encoding the protein having chalcone isomerase activity derived from the petunia, sharing the substrate with the present enzyme. The vector pSPB1342 was prepared as follows.

Total RNA was extracted from leaves of the petunia (cultivar: baccarat red, Sakata Seed Co.) using RNeasy Plant Mini Kit (Qiagen), and cDNA was synthesized from the RNA using Super Script™ First-Strand Synthesis System for RT-PCR (Invitrogen). Petunia CHI gene fragments of 0.6 kb and 0.8 kb were obtained from this cDNA by PCR using primers, BamHI-CHI-F (SEQ Id NO:49) and Sal-CHI-R (SEQ Id NO:50), Sal-CHI-F (SEQ Id NO:51) and EcoRI-CHI-R (SEQ Id NO:52), respectively. The resulting fragments were digested with BamH I and EcoR I, and Sal I and EcoR I, respectively to make the petunia CHI gene fragments. Meanwhile, pE2113 (Mitsuhara et al., Plant Cell Physiol., 37:45-59, 1996) has a cauliflower mosaic virus 35S (El235S) promoter where enhancer sequences are repeated and a nopaline synthase (nos) terminator. pUE6 was obtained by digesting pE2113 with SnaBI and inserting a BamH I linker. The pUE6 was digested with SacI to make a blunt end, and a Sal I linker (e.g., Takara) was inserted. This plasmid was digested with Hind III and EcoR I to yield DNA fragments. Among these fragments, the fragment having an El235S promoter was inserted at the Hind III-EcoR I site of pBINPLUS (vanEngelen et al., Plant Mol. Biol., 15:373, 1995), a binary vector for plant transformation. pSPB1601 was obtained by ligating an DNA fragment obtained by digesting this plasmid pSPB176 with BamH I and Sal I to the aforementioned two CHI gene fragments of the petunia. This pSPB1601 was digested with Asc I, and then dephosphorylated.

Subsequently, a cDNA fragment of about 1.5 kb was obtained by digesting the T170 gene inserted at a multiple cloning site, EcoR I-Xho I site of pBluescript II (sk⁻) (Stratagene) with BamH I (5' end side of cDNA) and Kpn I (3' end side of cDNA). A T170 gene expression cassette (pSPB1500) composed of an MAC1 promoter (Plant Mol. Biol., 15:373, 1990), the T170 gene and a mannopine synthetic enzyme (mas) terminator was constructed on the pUCAA, the plasmid that Pac I site of pUCAP (van Engelen et al., Transgenic research 4:288-290, 1995) had been substituted with Asc I linker. The cassette was placed between a portion of pUCAA cut with Hind III as 5' end and a portion of the pUCAA cut with EcoR I as 3' end.

BamHI-CHI-F:
(SEQ ID NO:49)
5'-tttggattctttatattcatgtaatcttagaac-3'

Sal-CHI-R:
(SEQ ID NO:50)
5'-tttgtcgacgtttacaacatcaggcccatttg-3'

Sal-CHI-F:
(SEQ ID NO:51)
5'-tttgtctactttatattcatgtaatcttagaac-3'

EcoRI-CHI-R:
(SEQ ID NO:52)
5'-tttgaattctattgattccagcactgcttcag-3'

The plasmid, pSPB1342 was prepared by recovering the whole T170 expression cassette constructed as the above by cut with Asc I and inserting at the site of the aforementioned pSPB1601 cut with Asc I in the same direction of the petunia CHI expression-inhibiting cassette, i.e., such that both left border sites (LB) of the binary vectors were upstream.

Subsequently, *Agrobacterium* with pSBP1342 was prepared, a leaf disk of the petunia (cultivar: PL) was transformed by an *Agrobacterium* method using the leaf disk. The transformation was performed according to the method known publicly (Plant J., 5:81, 1994).

Example 7

Expression of T170 and Change of Flavonoid Composition in Plant

The vector pSPB1342 prepared in Example 6 was introduced into *Agrobacterium tumefaciens* Agl0 (Lazo et al., Bio/Technology 9:963-967, 1991), and the petunia (cultivar: PL) leaf disk was transformed therewith by the *Agrobacterium* method using the leaf disk. Introduction of the plasmid into *Agrobacterium* and the transformation were performed according to the method known publicly (Plant J., 5:81, 1994). The flower color of the cultivar PL is white or pale pink because a flavonoid 3',5'-hydroxylase gene (Holton et al., Nature 366:276-279, 1993) and a flavonoid 3'-hydroxylase gene (Brugliera et al., Plant J., 19:441-451, 1999) are deleted. In the object of the experiment of the invention, the cultivar of the petunia is not limited to PL.

As in the above, 61 strains of independently transformed petunias were obtained. Total RNA was extracted from flower petals of the petunia using RNeasy Plant Mini Kit (Qiagen). A reverse transcription reaction of 1 μg of this total RNA was performed using Superscript First-Strand Synthesis System for RT-PCR (Invitrogen). Further, RT-PCR was performed using Ex Taq (Takara) by the method recommended by the manufacturer. The primers T170F and T170R were used for the amplification of T170 mRNA. The primers CHIF1 and CHIR1 were used for the amplification of petunia CHI mRNA. The sequences of the primers are as follows.

T170F:
5'-GAGCAAAGCACCGTTCGAGTT G-3'     (SEQ ID NO:22)

T170R:
5'-CTCCGTACATGATTGCAGAGAGCA-3'    (SEQ ID NO:23)

CHIF1:
5'-GCAAAAATGTCTCCTCCAGTGTCC-3'    (SEQ ID NO:24)

CHIR1:
5'-ACTTCTCAATGGCACGACCCTC-3'      (SEQ ID NO:25)

As a result, the T170 mRNA was detected in the petunia flower petals of 38 strains, and the reduction of petunia CHI mRNA was observed in 32 strains of the petunia.

The flower petals (0.5 g) of the petunia where the T170 mRNA had been detected was immersed in 50% acetonitrile containing 0.1% trifluoroacetic acid to extract flavonoid, which was then analyzed by high performance liquid chromatography (HPLC). As the condition for HPLC, the same condition as that in Example 5 using ODS-A-312 (150×6.0 mm) was employed. Under this condition, the glycoside having glucose at position 2' of chalcone and the glycoside having glucose at position 4' of chalcone were eluted at retention time of 19.89 min and 21.69 min, respectively. Three strains in the petunias which had expressed the T170 had a peak corresponding to the glycoside having glucose at position 2' of chalcone, and also had the same absorption spectrum. Furthermore, the extract of the petunia flower petals and the glycoside having glucose at position 2' of chalcone were analyzed by co-chromatography, and consequently, the peaks of the both were completely identical. From the above results, it could be shown that the glycoside having glucose at position 2' of chalcone had been synthesized by the expression of the T170, i.e., T170 encoded the functional glycosyltransferase on position 2' of chalcone. In the transformed petunia, although the amount of petunia CHI mRNA was decreased, the transcription thereof at a low level was observed.

Example 8

Construction of T170 Expression Vector for Plant

The glycoside having glucose at position 2' of chalcone was insufficiently accumulated only by the expression of the T170 and the inhibition of the petunia CHI gene. Therefore, the expression of flavanone 3 hydroxylase gene (F3H) (Britsh et al., European J. Biochemistry 217:745-754, 1993) or dihydroflavonol 4 reductase gene (DFR) (Beld et al., Plant Molecular Biology 13:491-502, 1989; Huits et al., Plant J., 6:295-310, 1994) of petunia was inhibited.

(8-1) Construction of Petunia F3H cDNA Double Strand Construct

A PhF3H-1 fragment was obtained by performing PCR using pSPB265 where a petunia F3H cDNA gene had been cloned in pBluescript II (sk−) as the template and using a set of an M13RV primer (SEQ ID NO:48) and a PhF3H-1-ClaI primer (SEQ ID NO:40). This PhF3H-1 fragment was cloned using Zero Blunt TOPO PCR Cloning Kit (Invitrogen), and then cut out with Sac I and Cla I to prepare a PhF3H-1' fragment of about 0.7 kb. Meanwhile, pSPB265 was digested with BamH I and Cla I and a fragment of about 0.9 kb was cut out to make PhF3H-2'. A blunt end was made at Asc I site of pUCAP (van Engelen et al., Transgenic research 4:288-290, 1995) and Pac I linker was inserted to construct a plasmid pUCPP. pUE6 was digested with EcoR I and Hind III. In the resulting fragments, a DNA fragment containing El235S promoter was inserted at a Hind III-EcoR I site of pUCPP. This plasmid was designated as pSPB540. pSPB1498 was constructed by ligating a DNA fragment of about 3.7 kb obtained by digesting pSPB540 with BamH I and Sac I to the PhF3H-1' and PhF3H-2' fragments. Consequently, this pSPB1498 employs a structure capable of transcripting dsF3H under the control of an El235S promoter and an NOS terminator.

Subsequently, a binary vector pSPB2201 where three genes, T170, dsCHI and dsF3H aligned in the same direction was constructed by introducing about 2.6 kb of gene cassette obtained by digesting pSPB1498 (dsPhF3H) with Pac I at the Pac I site of the binary vector pSPB1342 containing T170 and dsCHI. M13RV: 5'-caggaaacagctatgac-3' (SEQ ID NO:48) PhF3H-ClaI: 5'-tggttcctggatcagtgtgtcttttc-3' (SEQ ID NO:40)

(8-2) Construction of Petunia DFR cDNA Double Strand Construct

A plasmid pCGP1403 (WO 96/136716) containing the petunia DFR gene was digested with BamH I and Sca I, and Pvu II and Sac I to obtain 0.85 kb and 0.45 kb of fragments, respectively. A cassette composed of these both fragments which formed double strand RNA structures, an El235S promoter (Mitsuhara et al., Plant Cell Physiol., 37:49) and a mas terminator was inserted between Hind III-EcoR I of MCS of pBINPLUS (vanEngelen et al., Plant Mol. Biol., 15:373, 1995), a binary vector for the plant transformation to construct a plasmid pSPB532. This was digested with Pac I, and then dephosphorylated.

Subsequently, an about 2.5 kb fragment was obtained by digesting pSPB1601 containing the cassette composed of the El235S promoter, the petunia CHI gene with double strand RNA structure and the NOS terminator described in Example 6 with Hind III and EcoR I. This was inserted between Hind III-EcoR I of the vector pUCPP to construct pSFL5. This was cut with Pac I. The plasmid pSFL13 was obtained by inserting the 2.5 kb fragment obtained from pUCPP vector at the Pac I cut site of pSPB532 in the same direction as that of the petunia DFR expression-inhibiting cassette, i.e., such that LB sides of the vectors were upstream in both expression cassettes. Subsequently, this was digested with Asc I, and then dephosphorylated. On the plasmid vector, pUCAA described in Example 6, the T170 gene cassette composed of an MAC1 promoter (Comai et al., Plant Mol. Biol., 15:373, 1990), the T170 gene and the mannopine synthase gene terminator was cut with Asc I, and the fragment was cut out from the pUCAA vector to obtain about 3.5 kb of the fragment. This was inserted at the Asc I cut site of aforementioned pSFL13 so as to be in the same direction as those of petunia DFR and CHI expression-inhibiting cassettes to obtain a plasmid, pSFL14.

Example 9

Isolation of Chalcone Glycosyltransferase Gene, T128

There was a possibility that a chalcone glycosyltransferase gene other than T170 might be present in the carnation, and thus the search was continued. The nucleotide sequence of cDNA included in the plasmid which was designated as pT128 and the amino acid sequence thereof were shown in SEQ ID NOS: 14 and 15. The cDNA included in pT128 contained a gene T128 encoding a protein with molecular weight of 55.2 kDa composed of 489 amino acid residues. The amino acid sequence encoded by the T128 was compared with those of the glycosyltransferases already reported as described in Example 3. Consequently, it exhibited 54% identity with GT derived from the livingstone daisy, 24% identity with 5GT derived from the *verbena* and 27% identity with the T170 in amino acid sequences.

Example 10

Expression and Activity Measurement of T128 Gene in *E. coli*

The expression of the T128 gene in *E. coli* was performed using The QIA expressionist (Qiagen) which was the same as the method described in Example 4. First, to introduce an Nco I recognition sequence at 5' side of an initiation codon of the glycosyltransferase gene on T128, the PCR reaction as with Example 4 was performed using the primer T128-NcoI shown below and M13 M4 shown in Example 4.

```
T128-NcoI:
5'-ACAATTTCAGCCATGGGCAC-3'      (SEQ ID NO:26)
```

The resulting PCR product was subcloned into pCR2.1 TOPO vector (Invitrogen) according to the method recommended by the manufacturer. The plasmid obtained in this way was designated as pTOPO-T128. It was confirmed by sequencing that there was no error in the PCR reaction. A plasmid pSPB1441 was obtained by ligating an about 1.8 kb fragment obtained by treating the pTOPO-T 128 with restriction enzymes Nco I and Kpn I to the same sites of the pQE-61 vector (Qiagen). Competent high JM109 (Toyobo) was transformed with pSPB1441.

This transformed *E. coli* strain was cultured and a crude enzyme solution was obtained by the methods described in Example 5. Using this, the glycosyltransfer activity was measured using the chalcone as the substrate. An extracted solution of *E. coli* which had expressed the glycosyltransferase gene derived from T128 was reacted, and consequently new substances eluted at 19.89 min and 21.69 min were detected in addition to THC (retention time: 27.3 min). It was confirmed that the former was the glycoside having glucose at position 2' of THC and the latter was the glycoside having glucose at position 4' of THC by comparing the retention time of each standard preparation. These are believed to be the products produced by the glycosyltransferase derived from T128 because these were not detected when a crude extract solution similarly prepared from *E. coli* in which the pQE-61 vector alone had been expressed was reacted. From the above results, it has been confirmed that the glycosyltransferase derived from T128 has the activity to glycosyltransfer glucose to the hydroxyl groups at positions 2' and 4' of THC.

Example 11

Construction of T128 Expression Vector for Plant

In order to demonstrate the function of the gene product of the glycosyltransferase on position 2' of chalcone derived from T128 in the plant, a co-expression binary vector (pSPB2108) was constructed. The vector allowed to express T128 whereas the expression of CHI-A gene encoding the protein having chalcone isomerase activity derived from the petunia, sharing the substrate with the present enzyme was inhibited. The vector pSPB2108 was prepared as with Example 6 as follows.

First, the pSPB1601 was digested with Asc I, and then dephosphorylated.

Subsequently, a T128 cDNA fragment was obtained by digesting the T128 gene inserted at a multiple cloning site of pBluescript II (sk⁻) with BamH I (5' end side of cDNA) and Kpn I (3' end side of cDNA). Subsequently, on the plasmid vector pUCAA, the T128 gene expression cassette composed of the MAC1 promoter, the T128 gene and the mannopine synthase gene terminator was constructed using BamH I cut site and Kpn I site of the pUCAA vector at the 5' end and the 3' end, respectively. This whole T128 expression cassette was cut out from the pUCAA vector by cutting with Asc I.

The plasmid pSPB2108 was obtained by inserting the expression cassette cut out from the pUCAA with Asc I at Asc I cut site of the aforementioned pSPB1601 in the same direction as that of the petunia CHI expression-inhibiting cassette, i.e., such that the LB side of the vectors in both cassettes were upstream.

Example 12

Isolation of Chalcone Glycosyltransferase Gene, CGT93

Using the T170 as a probe, 24,000 plaques of the carnation flower petal library were screened. A plasmid, pCGT93 was obtained by screening. The cDNA included in the pCGT93 contained a gene, CGT93 of 1443 bp encoding a protein with molecular weight of 52.8 kDa composed of 481 amino acid residues. The amino acid sequence encoded by the CGT93 was compared with those of the glycosyltransferases already reported as described in Example 3. Consequently, it exhibited 26% identity with GT derived from the livingstone daisy, 23% identity with 5GT derived from the *verbena*, and 63% identity with the T170 and 25% identity with the T128 in amino acid sequences. The nucleotide sequence comprising the gene included the pCGT93 and the amino acid sequence encoded by the nucleotide sequence were shown in SEQ ID NOS: 16 and 17.

Example 13

Expression and Activity Measurement of CGT93 Gene in *E. coli*

The expression of the CGT93 gene in *E. coli* was performed using The QIA expressionist (Qiagen) which was the same as the method described in Example 4. First, to introduce the Nco I recognition sequence at 5' side of the initiation codon of the glycosyltransferase gene on the CGT93, the PCR reaction as with Example 4 was performed using the primers A93-75BspHI and A93-75-BglII shown below.

```
A93-75BspHI:
5'-ACAGGATCATGACTTCAGGG-3'         (SEQ ID NO:27)

A93-75-BglII:
5'-GGAAGATCTAATATACGTGAGTAC-3'     (SEQ ID NO:28)
```

The resulting PCR product was subcloned into a pCR-Blunt II-TOPO vector (Invitrogen) according to the method recommended by the manufacturer. The obtained plasmid was designated as the plasmid pSPB1469. It was confirmed by sequencing that there was no error in the PCR reaction. This pSPB1469 was treated with restriction enzymes, BspH I and Bgl II, and the resulting about 1.8 kb fragment was ligated to the cut sites with Nco I and Bgl II of the pQE-61 vector to construct a plasmid, pSPB1470. Competent high JM109 was transformed with this pSPB1470.

This transformed *E. coli* strain was cultured and a crude enzyme solution was obtained by the methods described in Example 5. Using this, the glycosyltransfer activity was measured by the methods described in Example 5 using the chalcone as the substrate.

The extracted solution of *E. coli* in which the glycosyltransferase gene derived from CGT93 had been expressed was reacted, and consequently, a new substance eluted at 19.89 min was detected in addition to THC (retention time: 27.3 min). This is believed to be a product produced by the glycosyltransferase derived from the CGT93 because this was identical to the retention time of the glycoside having glucose at position 2' of THC and no new substance was detected in the reacted crude extracted solution similarly prepared from *E. coli* in which the pQE-61 vector alone had been expressed.

From the above results, it has been confirmed that the glycosyltransferase derived from the CGT93 has the activity to transfer glucose to the hydroxyl group at position 2' of THC.

Example 14

Construction of Expression Vector Containing CGT93 for Plants

In order to demonstrate the function of the gene product of the glycosyltransferase on position 2' of chalcone derived from the CGT93 in the plant, a co-expression binary vector (pSPB1494) was constructed. The vector allowed to express the CGT93 whereas to inihibit the expression of CHI-A gene encoding the protein having the chalcone isomerase activity derived from the petunia, sharing the substrate with the present enzyme. The vector pSPB1494 was prepared as with Example 6 as follows.

First, the pSPB1601 was digested with Asc I, and then dephosphorylated.

Subsequently, the CGT93 gene inserted at the multiple cloning site of pBluescript II (sk⁻) was digested with Xho I (3' end side of cDNA), then blunted using DNA Blunting Kit (Takara), and further digested with BamH I (5' end side of cDNA) to obtain a CGT93 cDNA fragment. A plasmid pSPB184 composed of the MAC1 promoter and the mannopine synthase gene terminator was digested with Kpn I, then blunted using DNA Blunting Kit, and further digested with BamH I. The both of BamH I digested fragments above were inserted at this BamH I site on the plasmid vector pUCAA. A gene expression cassette pSPB1493 composed the MAC1 promoter, the CGT93 gene and the mannopine synthase gene terminator, and having a BamH I cut site of the vector at the 5' end and a Kpn I site at the 3' end was constructed.

The cassette pSPB1493 constructed in this way was cut out with Asc I as the whole CGT93 expression cassette from the vector pUCAA, and inserted at the aforementioned Asc I cut site of the pSPB1601 in the same direction as that of the petunia CHI expression-inhibiting cassette, i.e., such that the LB sides of the vectors were upstream in both expression cassettes to construct a plasmid which was designated as pSPB1494.

Example 15

Preparation of Subtraction Library

Poly-A+RNA was obtained from buds, flower petals and leaves of the yellow carnation by the method described in Example 1. A cDNA library where genes expressed in the flower petal were concentrated was prepared by the method recommended by the manufacturer using Clontech PCR-Select cDNA Subtraction Kit (Clontech). As a result of random sequencing, 16 clones having the homology to GC were obtained. These GT homolog clones obtained by subtraction did not have the full length. Therefore, 24,000 clones from the flower petal cDNA library were screened again using the GT homolog fragments as probes. The screening was performed according to the method described in Example 2.

Example 16

Isolation of Chalcone Glycosyltransferase Gene, S6B11

A nucleotide sequence of cDNA included in a plasmid designated as pS6B11 which was a clone obtained by the subtraction in Example 15 and an amino acid sequence thereof were shown in SEQ ID NOS 18 and 19 in Sequence Listing. The cDNA included in the pS6B11 contained a gene, S6B11 of 1449 bp encoding a protein with molecular weight of 54.4 kDa composed of 483 amino acid residues. The sequence was compared with those of the glycosyltransferases already reported as described in Example 3. Consequently, it exhibited 60% identity with GT derived from the livingstone daisy, 26% identity with 5GT derived from the *verbena*, as well as 27%, 54% and 27% identity with the T170, T128 and CGT93, in amino acid sequences.

Example 17

Construction of S6B11 Expression Vector for Plants

In order to demonstrate the function of the gene product of the chalcone glycosyltransferase derived from S6B11 in the plant, a co-expression binary vector (pSPB1335) was constructed. The vector allowed to express the S6B11 whereas to inhibit the expression of CHI-A gene encoding the protein having chalcone the isomerase activity derived from the petunia, sharing the substrate with the present enzyme. The vector pSPB1335 was prepared as with Example 6 as follows.

First, the pSPB1601 was digested with Asc I, and then dephosphorylated.

Subsequently, a S6B11 cDNA fragment was obtained by digesting the S6B11 gene inserted at the multiple cloning site of pBluescript II (sk⁻) with BamH I (5' end side of cDNA) and Kpn I (3' end side of cDNA). Subsequently, an S6B11 gene expression cassette composed of the MAC1 promoter, the S6B11 gene and the mannopine synthase gene terminator was constructed on the plasmid vector pUCAA at the cut site of Bam H I as 5' end and the cut site of Kpn I as the 3' end. This S6B11 expression cassette was entirely cut out with Asc I from the vector pUCAA.

The S6B11 expression cassette cut out as the above was inserted at the aforementioned Asc I cut site of the pSPB1601 in the same direction as that of the petunia CHI expression-inhibiting cassette, i.e., such that the LB sides of the vectors were upstream in both expression cassettes to construct a plasmid which was designated as pSPB1335.

Example 18

Expression of S6B11 and Change of Flavonoid Composition in Plant

As described in Example 7, the pSPB1335 was introduced into *Agrobacterium tumefaciens* Ag10, and the petunia PL strains were transformed therewith.

As a result, 27 strains of independently transformed petunias were obtained. The RT-PCR reaction as with Example 7 was performed using RNA of the petunia flower petals. The primers, S6B11-RT-F and S6B11-RT-R were used for the amplification of S6B11 mRNA, and the same CHIF1 and CHIR1 as those in Example 7 were used for the amplification of CHI mRNA. The sequences of the primers are as follows.

```
S6B11-RT-F:
5'-GTAATCCGCTCATCAATGTGGAG-3'      (SEQ ID NO:29)

SGB11-RT-R:
5'-AGCAAATGGTTCGTCGTCAGAC-3'       (SEQ ID NO:30)
```

As a result, the S6B11 mRNA was detected in the flower petals in 24 petunia strains, and the reduction of CHI mRNA was observed in 11 petunia strains. Flavonoid was extracted from the flower petals of petunia in which the S6B11 mRNA had been detected, as is the case with Example 7, and analyzed by high performance liquid chromatography based on a methanol solvent using ODS-A-312. Among the petunias which had expressed the S6B11, 4 strains had a peak equivalent to the peak of the glycoside having glucose at position 2' of chalcone and the same absorption spectrum. Further, an extract from the flower petals of petunia in which S6B11 had been expressed and the glycoside having glucose at position 2' of chalcone were analyzed, and consequently both peaks were completely identical. The above could prove that the glycoside having glucose at position 2' of chalcone was synthesized by the expression of S6B11, i.e., the S6B11 encoded the functional glycosyltransferase on position 2' of chalcone in the plant. In the transformed petunia, although the amount of petunia CHI mRNA was decreased, the transcription at a low level was observed.

Example 19

Isolation of Chalcone Glycosyltransferase Gene, S12A2

The clone, pS12A2-a obtained by the subtraction in Example 15 deleted the 5' region. An about 0.4 kb fragment (pS12A2-b) was TA-cloned by 5'-RACE using S12A2-RT, four primers, S12A2-S1, S12A2-A1, S12A2-S2 and S12A2-A2, and 5'-full RACE Core Set (Takara). The primers are shown below.

```
S12A2-NcoI:
5'-ACCAGACCATGGGTGCTG-3'           (SEQ ID NO:31)

S12A2-S1:
5'-GAGATTGCAATGGGCATCC-3'          (SEQ ID NO:32)

S12A2-S2:
5'-GTGGCCGACATGTTTTACCC-3'         (SEQ ID NO:33)

S12A2-A1:
5'-GCATTCTCACAACCCTCAGG-3'         (SEQ ID NO:34)

S12A2-A2:
5'-TCTGTTACCCGTGTCAACTGC-3'        (SEQ ID NO:35)
```

A fragment amplified by PCR with the S12A2-NcoI and S12A2-A2 using the pS12A2-b as the template was further TA-cloned again (pS12A2-c). A vector was constructed by introducing a fragment obtained by digesting pS12A2 with Nde I and Kpn I, wherein the fragment had been inserted, at the same site of pS12A2-c. Then a clone which contained the full length (pS12A2-d) was obtained. A nucleotide sequence of cDNA included in this plasmid and an amino acid sequence thereof were shown in SEQ ID NOS 20 and 21 in Sequence Listing. The cDNA included in pS12A2-d contained a gene S12A2 of 1458 bp encoding a protein with molecular weight of 55.0 kDa composed of 486 amino acid residues. The sequence was compared with those of the glycosyltransferases already reported as described in Example 3. Consequently, it exhibited 57% identity with GT derived from the livingstone daisy, 25% identity with 5GT derived from the verbena, as well as 27%, 52%, 27% and 67% identity with the T170, T128, CGT93 and S6B11, respectively in amino acid sequences.

Example 20

Expression and Activity Measurement of S12A2 Gene in E. Coli

Expression of the S12A2 gene in E. coli was performed using The QIA expressionist (Qiagen) according to the same method described in Example 4. The pS12A2-d in Example 19 was digested with Nco I and Kpn I, and ligated to the same site of the pQE-61 to construct pSPB1439. Competent high JM109 (Toyobo) was transformed with the pSPB1439.

This transformed E. coli strain was cultured by the methods described in Example 5 and a crude enzyme solution was obtained. Using this, the glycosyltransfer activity was measured using the chalcone as the substrate by the methods described in Example 5.

The extracted solution of E. coli in which the glycosyltransferase gene derived from the S12A2 had been expressed was reacted, and consequently, a new substance eluted at 19.89 min was detected in addition to THC (retention time: 27.3 min). This is believed to be a product produced by the glycosyltransferase derived from the S12A2 because no new substance was detected in the reacted crude extracted solution similarly prepared from E. coli in which the pQE-61 vector alone had been expressed. From the above results, it has been confirmed that the glycosyltransferase derived from the S12A2 has the activity to transfer glucose to the hydroxyl group at position 2' of THC.

Example 21

Construction of Expression Vector of S12A2 for Plants

In order to demonstrate the function of the gene product of the chalcone glycosyltransferase derived from the S12A2 in the plant, a co-expression binary vector (pSPB1478) was constructed. The vector allowed to express the S12A2 whereas to in inhibit the expression of CHI-A gene encoding the protein having the chalcone isomerase activity derived from the petunia, sharing the substrate with the present enzyme. The vector pSPB1478 was prepared as with Example 6 as follows.

First, the pSPB1601 was digested with Asc I, and then dephosphorylated.

Subsequently, an S12A2 cDNA fragment was obtained by digesting the S12A2 gene inserted at the multiple cloning site of pBluescript II (sk⁻) with BamH I (5' end side of cDNA) and Kpn I (3' end side of cDNA). Subsequently, an S12A2 gene expression cassette composed of the MAC1 promoter, the S12A2 gene and the mannopine synthase gene terminator was constructed on the plasmid vector pUCAA at the cut site of BamH I as the 5' end and the cut site of Kpn I as the 3' ends. This S12A2 expression cassette was entirely cut out with Asc I from the vector pUCAA.

The S12A2 expression cassette cut out as the above was inserted at the aforementioned Asc I cut site of the pSPB1601 in the same direction as that of the petunia CHI expression-inhibiting cassette, i.e., such that the LB sides of the vectors were upstream in both expression cassettes to construct a plasmid which was designated as pSPB1478.

Example 22

Expression of T170 in Plants 2

As described in Example 7, the pSFL14 was introduced into *Agrobacterium tumefaciens* Ag10, and the petunia PL strains and baccarat red strains were transformed therewith. Likewise, the PL strains and baccarat red strains were also transformed with the pSPB2201.

Example 23

Construction of T170 Expression Vector for Plants

In order to express the T170 and accumulate the chalcone glycoside in plants, e.g., torenia and *verbena* other than petunia, a co-expression vector to inhibit flavanone 3 hydroxylase (F3H) derived from the torenia was constructed for the torenia. For the *verbena*, a co-expression vector where CHI derived from the *verbena* (Tapian, registered trademark) was inhibited and a co-expression vector where expression of both CHI and F3H (Hanatemari, registered trademark) genes was inhibited were constructed.

(23-1) Construction of Torenia F3H cDNA Double Strand Construct (dsF3H)

A cDNA library (Molecular Breeding 6:239, 2000) of torenia flower petals were screened using the petunia F3H gene as a probe by the method described in Example 2 to isolate a torenia F3H gene.

PCR was performed by using pSPB266 where a cDNA gene of torenia F3H was cloned at pBluescript II (sk−) as a template and using a set of an M13RV primer (SEQ ID NO:48) and a ThF3H-SalI1 primer (SEQ ID NO:41) to obtain a ThF3H-1 fragment. Likewise, the PCR was performed by using a set of a reverse primer and ThF3H-SalI2 primer (SEQ ID NO:42) to obtain a ThF3H-2 fragment. The ThF3H-1 fragment and the ThF3H-2 fragment were TA-cloned using TOPO TA cloning Kit (Invitrogen), and then the former was cut out with Sac I and Sal I to yield an about 0.75 kb fragment which was designated as ThF3H-1'. Meanwhile, the latter was cut out with BamH I and Sal I to obtain an about 0.9 kb fragment which was designated as ThF3H-2'. DNA containing the promoter, obtained by digesting the pUE6 with Hind III and EcoR I, was inserted at Hind III and EcoR I sites of the pUCAA. An about 3.8 kb DNA fragment obtained by digesting this with BamH I and Sac I was ligated to the ThF3H-1' and ThF3H-2' fragments to construct pSFL308. Consequently, this pSFL308 employs the structure having the dsF3H and the NOS terminator downstream of the El2355 promoter. An about 2.7 kb fragment obtained by digesting pSFL308 (dsThF3H) with Asc I was blunted, and then introduced at SamI site of pBINPLUS to construct pSPB2218. About 3.7 kb of the T170 gene cassette sandwiched between the Mac promoter and the mas terminator was cut out with Asc I from the pSPB1342, and introduced at Asc I site of the pSPB2218 to construct the binary vector in which two genes of T170 and dsF3H were loaded in the same direction (pSPB2223).

```
ThF3H-SalI1:
5'-ttctctgtcgacgcccattgcc-3'      (SEQ ID NO:41)

ThF3H-SalI2:
5'-cgccgtgtcgactcgcttgaag-3'      (SEQ ID NO:42)
```

(23-2) Construction of *verbena* (Hanatemari, Registered Trademark) dsF3H

A cDNA library (Plant Cell Physiol., 44:s122, 2003) of *verbena* flower petals were screened using the petunia F3H gene as a probe by the method described in Example 2 to isolate a *verbena* F3H gene.

A plasmid pSPB9 where a cDNA gene of *verbena* F3H was cloned into pBluescript II (sk−) was digested with BstX I, then blunted, and partially digested with BamH I to recover an about 1.1 kb of gene fragment, which was designated as HaF3H-1. The pSPB9 was digested with Sac I and Hae II to recover an about 0.7 kb gene fragment, which was designated as HaF3H-2. An about 3.8 kb DNA fragment obtained by digesting the pSPB540 with BamH I and Sac I was ligated to the HaF3H-1 and HaF3H-2 fragments to construct pSPB2501. This pSPB2501 employs the structure having the dsF3H and the NOS terminator downstream of the El235S promoter.

(23-3) Construction of *verbena* (Tapian, Registered Trademark) dsCHI

A cDNA library (Plant Cell Physiol., 44:s122, 2003) of *verbena* flower petals were screened using the petunia CHI gene as a probe by the method described in Example 2 to isolate a *verbena* CHI gene.

PCR was performed by using the pSPB2109 where a cDNA gene of *verbena* CHI was cloned into pBluescript II (sk−) as the template and using a set of an M13RV primer (SEQ ID NO:48) and a TpCHI-XbaI2 primer (SEQ ID NO:45) to obtain a TpCHI-1 fragment. Likewise, the PCR was performed by using a TpCHI-SalI primer (SEQ ID NO:43) and a TpCHI-XbaI1 primer (SEQ ID NO:44) to yield a TpCHI-2 fragment. The TpCHI-1 fragment and the TpCHI-2 fragment were cloned using Zero Blunt TOPO PCR Cloning Kit (Invitrogen), and then the former was cut out with BamH I and Xba I to yield an about 0.68 kb fragment, which was designated as TpCHI-1'. Meanwhile, the latter was cut out with Xba I and Sal I to obtain an about 0.5 kb fragment, which was designated as TpCHI-2'. A DNA fragment where a GUS gene region had been eliminated by cutting out with BamH I and Sal I from the pSPB176 was ligated to the TpCHI-1' and TpCHI-2' fragments to construct pSPB1486. Consequently, the pSPB1486 employs the structure having the dsCHI and the NOS terminator downstream of the El235S promoter. This pSPB1486 was digested with Pac I, and then a PacI-FseI adaptor where two oligo DNA of PacI-FseIF (SEQ ID NO:46) and PacI-FseIR (SEQ ID NO:47) had been annealed was introduced to prepare pSPB2508 where a Fse I site was newly introduced.

```
TpCHI-SalI:
5'-acgcagaaaaaagtcgactg-3'        (SEQ ID NO:43)

TpCHI-XbaI1:
5'-gaggtgattgggtctagag-3'         (SEQ ID NO:44)

TpCHI-XbaI2:
5'-atttctagagcaggtccgacaat-3'     (SEQ ID NO:45)

PacI-FseIF:
5'-taactgcactgaggccggccagat-3'    (SEQ ID NO:46)

PacI-FseIR:
5'-ctggccggcctcagtgcagttaat-3'    (SEQ ID NO:47)
```

(23-4) Construction of *verbena* (Hanatemari, Registered Trademark) dsF3H+ *verbena* (Tapian, Registered Trademark) dsCHI A 2.9 kb gene fragment obtained by digesting the pSPB2501 with Pac I was introduced at Pac I site of the pSPB2508 to construct pSPB2504.

(23-5) Construction of T170 Gene Expression Vector (T170+dsCHI) for *verbena*

A binary vector pSPB1287 where two gene cassettes of T170 and dsCHI was loaded was constructed by introducing the 3.7 kb T170 gene cassette produced by cutting out pSPB1500 in Example 6 with Asc I to the Asc I site of the pSPB1486.

(23-6) Construction of T170 Gene Expression Vector (T170+dsCHI+dsF3H) for *verbena* 2

An adaptor, EcoFse1R where oligo DNA of EcoFse1 (SEQ ID NO:57) and EcoFseR (SEQ ID NO:58) had been annealed was introduced to the EcoR I site of pUC19, and then an adaptor HinFse3R where oligo DNA of HinFseR (SEQ ID NO:59) and HinFseR3 (SEQ ID NO:60) had been annealed was introduced to the Hind III site to construct a vector (pSPB1838) where two Fse I sites were introduced to both end sides of the multiple cloning site of the pUC19. A plasmid pSPB2505 was constructed by blunting the 3.7 kb T170 gene cassette produced by cutting out pSPB1500 in Example 6 with Asc I, and then inserting at a blunted site after digesting the pSPB1838 with Hind III and EcoR I. This operation enables to cut out the T170 gene cassette using Fse I.

The 3.7 kb T 170 gene cassette obtained by digesting pSPB2505 with Fse I was introduced to the Fse I site of the pSPB2504 to construct pSPB2507. As a result, the pSPB2507 employs the structure where the three gene cassettes of dsCHI, T170 and dsF3H are aligned in the same direction.

Example 24

Expression of T170 in *verbena*

The plasmid pSPB1287 was introduced into *Agrobacterium tumefaciens* Ag10 (Biotechnology), and the *verbena* (cultivar: Hanatemari scarlet) was transformed according to Tamura's method (Tamura et al., Plant Cell Rep., 21:459-466, 2003).

According to the above, 7 strains of independently transformed *verbena* were obtained. The RT-PCR reaction was performed using RNA of the *verbena* flower petals according to the same manner described in Example 7. The same primers T170F and T170R as those in Example 7 were used for the amplification of T170 mRNA, and the expression amount of *verbena* CHI mRNA was confirmed by the amplification of an about 0.5 kb gene fragment using the TpCHI-SalI primer (SEQ ID NO:43) and the TpCHI-XbaI1 primer (SEQ ID NO:44). As a result, the T170 mRNA was detected in the *verbena* flower petals of 7 strains, and the reduction in the expression amount of the *verbena* CHI mRNA was observed in the *verbena* flower petals of 3 strains. It could be confirmed that the flower color of the flower petals of one strain (SaT170#7) in 7 strains in which the expression of T170 had been confirmed was paler than control red color and was slightly tinged with yellow.

Example 25

Expression of T128 and Change of Flavonoid Composition in Plants

As described in Example 7, the pSPB2108 prepared in Example 11 was introduced into *Agrobacterium tumefaciens*-Ag10, and the petunia PL strains were transformed therewith.

As a result, 37 strains of independently transformed petunias were obtained. The RT-PCR reaction as with Example 7 was performed using RNA of petunia flower petals. The primers, T128-F (SEQ ID NO:38) and T128-R (SEQ ID NO:39) were used for the amplification of T128 mRNA, and the same CHIF1 and CHIR2 as those in Example 7 were used for the amplification of CHI. The sequence of each primer is as follows.

```
T128-F:
5'-acgagttagaacccgagtatgctg-3'    (SEQ ID NO:38)

T128-R:
5'-cagtgtgtcacgaatcctcctacg-3'    (SEQ ID NO:39)
```

As a result, the T128 mRNA was detected in the flower petals in 19 petunia strains, and the reduction of CHI mRNA was observed in 26 petunia strains. Flavonoid was extracted from the flower petals of petunia in which the T128 m RNA had been detected according to the same manner described in Example 7, and analyzed by HPLC in the same method as that in Example 5. Among petunias which had expressed T128, 2 strains had a peak equivalent to the peak of the glycoside having glucose at position 2' of chalcone and the same absorption spectrum. Further, an extract from the flower petals of petunia in which the T128 had been expressed and the glycoside having glucose at position 2' of chalcone were analyzed by co-chromatography, and consequently both peaks were completely identical. The above could prove that the glycoside having glucose at position 2' of chalcone was synthesized by the expression of T128, i.e., the T128 encoded the functional glycosyltransferase on position 2' of chalcone in the plant.

Example 26

Construction of T128 Expression Vector for Plant 2

(26-1) T128+Petunia dsCHI+dsF3H

An about 2.6 kb gene cassette obtained by digesting the pSPB1498 (dsPhF3H) with Pac I was introduced to the Pac I site of the binary vector, pSPB2108 having the T128 and dsCHI to construct a vector, pSPB1499 having three genes of the T128, dsCHI and dsF3H together.

(26-2) T128+Torenia dsF3H

The about 3.7 kb T128 gene cassette sandwiched between the Mac promoter and the mas terminator was cut out with Asc I from the pSPB2108, and introduced to the Asc I site of the pSPB2218 prepared in Example 23 to construct a binary vector where two genes of the T128 and dsF3H were loaded in the same direction (pSPB2224).

Example 27

Expression of T128 in Plant

As described in Example 7, the pSPB1499 was introduced into *Agrobacterium tumefaciens* Ag10, and the petunia PL strains were transformed therewith.

Example 28

Construction of CGT93 Expression Vector for Plant 2

(28-1) CGT93+Petunia dsCHI+dsF3H

An about 2.6 kb gene cassette obtained by digesting the pSPB1498 (dsPhF3H) with Pac I was introduced to the Pac I site of the binary vector pSPB1494 having the CGT93 and dsCHI to construct a binary vector pSPB2202 having three genes of the CGT93, dsCHI and dsF3H together.

(28-2) CGT93+Torenia dsF3H

The about 3.7 kb CGT93 gene cassette sandwiched between the Mac promoter and the mas terminator was cut out with Asc I from pSPB1494, and introduced to the Asc I site of the pSPB2218 prepared in Example 23 to construct a binary vector, where two genes of the CGT93 and dsF3H were loaded in the same direction (pSPB2225).

Example 29

Expression of CGT93 in Plants

As described in Example 7, the pSPB1494 was introduced into *Agrobacterium tumefaciens* Agl0, and the petunia PL strains were transformed therewith. The petunia PL strains and baccarat red strains were transformed with the pSPB2202.

Example 30

Construction of S6B11 Expression Vector for Plant (30-1) S6B11+Petunia dsCHI+dsF3H An about 2.6 kb gene cassette obtained by digesting pSPB1498 (dsPhF3H) with Pac I was introduced to the Pac I site of the binary vector pSPB1335 having the S6B11 and dsCHI to construct a binary vector pSPB2205 having three genes of the S6B11, dsCHI and dsF3H together.

(30-2) S6B11+Torenia dsF3H

The about 3.7 kb S6B11 gene cassette sandwiched between the Mac promoter and the mas terminator was cut out with Asc I from the pSPB1335, and introduced to the Asc I site of the pSPB2218 prepared in Example 23 to construct a binary vector where two genes of the S6B11 and dsF3H were loaded in the same direction (pSPB2226).

Example 31

Expression of S6B11 in Plant 2

As described in Example 7, the pSPB2205 was introduced into *Agrobacterium tumefaciens* Agl0, and the petunia PL strains were transformed therewith.

Example 32

Construction of S12A2 Expression Vector for Plant 2

(32-1) S12A2+Petunia dsCHI+dsF3H

An about 2.6 kb gene cassette obtained by digesting the pSPB1498 (dsPhF3H) with Pac I was introduced to the Pac I site of the binary vector pSPB1478 having the S12A2 and dsCHI to construct a binary vector pSPB2206 having three genes of the S12A2, dsCHI and dsF3H together.

(32-2) S12A2+Torenia dsF3H

The about 3.7 kb S12A2 gene cassette sandwiched between the Mac promoter and the mas terminator was cut out with Asc I from the pSPB2206, and introduced to the Asc I site of the pSPB2218 prepared in Example 23 to construct a binary vector where two genes of the S12A2 and dsF3H were laded in the same direction (pSPB2227).

Example 33

Expression of S12A2 in Plant

As described in Example 7, the pSPB1478 prepared in Example 21 was introduced into *Agrobacterium tumefaciens* Agl0, and the petunia PL strains were transformed therewith. The PL strains were also transformed with the pSPB2206.

Example 34

Construction of Cyclamen Flower Petal cDNA Library

A cDNA library was constructed from 5 g of fresh flower petals of the yellow cyclamen by the same method as that in Example 1. The resulting library was composed of $1.75 \times 10^6$ plaque forming units (pfu).

Example 35

Isolation of Chalcone Glycosyltransferase Gene, YCy3-12

Using the T170 as a probe, 24,000 plaques of the cyclamen flower petal library were screened. A plasmid, pYCy3-12 was obtained. cDNA included in the pYCy3-12 contained a gene, YCy3-12 of 1446 bp encoding a protein with molecular weight of 54.3 kDa composed of 482 amino acid residues. The amino acid sequence encoded by YCy3-12 was compared with those of the glycosyltransferases already reported as described in Example 3. Consequently, it exhibited 28% identity with GT derived from the livingstone daisy, 24% identity with 5GT derived from the *verbena*, as well as 46%, 28%, 46%, 28% and 27% identity with the T170, T128, CGT93, S6B11 and S12A2 in amino acid sequences, respectively. The nucleotide sequence including the gene contained in pYCy3-12 and the amino acid sequence encoded by the nucleotide sequence are shown in SEQ ID NOS 55 and 56, respectively in Sequence Listing.

Example 36

Expression and Activity Measurement of YCy3-12 in *E. Coli*

Expression of YCy3-12 gene in *E. coli* was performed using The QIA expressionist (Qiagen) according to the same method described in Example 4. First, to introduce the Nco I recognition sequence at 5' side of the initiation codon of the glycosyltransferase gene on the YCy3-12, PCR reaction was performed using the primers, YCy-3-12P1 (SEQ ID NO:53) and YCy-3-12P2 (SEQ ID NO:54) shown below as was the case with Example 4.

```
YCy-3-12P1:
5'-ccccatggagagggcagagctagcctttca-3' (SEQ ID NO:53)

YCy-3-12P2:
5'-aaagcttcacgaagagcgattgagtacttc-3' (SEQ ID NO:54)
```

The resulting PCR product was subcloned into a pCR-Blunt II-TOPO vector (Invitrogen) according to the method recommended by the manufacturer. The plasmid obtained in this way was designated as the plasmid pTOPO-YCy3-12. It was confirmed by sequencing that there was no error in the PCR reaction. An about 1.8 kb fragment obtained by treating pTOPO-YCy3-12 with restriction enzymes, Nco I and Hind III was ligated to the Nco I and Hind III sites of the pQE-61 vector to construct a plasmid, pQE-YCy3-12. Competent high JM109 was transformed with the pQE-YCy3-12.

This transformed *E. coli* strain was cultured and a crude enzyme solution was obtained by the methods described in Example 5. Using this, the glycosyltransfer activity was measured using the chalcone as the substrate by the methods described in Example 5.

The extracted solution of *E. coli* in which the glycosyltransferase gene derived from the YCy3-12 had been expressed was reacted, and consequently, a new substance eluted at 19.89 min was detected in addition to THC (retention time: 27.3 min). This is believed to be a product produced by the glycosyltransferase derived from the YCy3-12 because no new substance was detected in the reacted crude extracted solution similarly prepared from *E. coli* in which the pQE-61 vector alone had been expressed. From the above results, it has been confirmed that the glycosyltransferase derived from the YCy3-12 has the activity to transfer glucose to the hydroxyl group at position 2' of THC.

INDUSTRIAL APPLICABILITY

The present invention is applied to industries related to flowers and ornamental plants, horticulture, plant breeding, agriculture and biotechnology.

Free Text in the Sequence Listing:
SEQ ID NO:3, *Ipomoea purpurea* 3GGT PN3GGTF
SEQ ID NO:4, *Ipomoea purpurea* 3GGT PN3GGTR
SEQ ID NO:5, *Gentiana scabra* 3GT GT3GTF
SEQ ID NO:6, *Gentiana scabra* 3GT GT3GTR
SEQ ID NO:7, *Verbena hybrida* 5GT H5GTF
SEQ ID NO:8, *Verbena hybrida* 5GT H5GTR
SEQ ID NO:9, *Scutellaria baicalensis* GT SBGTF
SEQ ID NO:10, *Scutellaria baicalensis* GT SBGTR
SEQ ID NO:11, T170-NcoI PCR primer
SEQ ID NO:12, M13M4 PCR primer
SEQ ID NO:13, An amino acid sequence of a protein having an activity to transfer glucose to sugar at position 3 of flavonoids
SEQ ID NO:22, T170F PCR primer
SEQ ID NO:23, T170R PCR primer
SEQ ID NO:24, CHIF1 PCR primer
SEQ ID NO:25, CHIR1 PCR primer
SEQ ID NO:26, T128-NcoI PCR primer
SEQ ID NO:27, A93-75 BspHI PCR primer
SEQ ID NO:28, A93-75-BglII PCR primer
SEQ ID NO:29, S6B11-RT-F PCR primer
SEQ ID NO:30, S6B11-RT-R PCR primer
SEQ ID NO:31, S12A2-NcoI PCR primer
SEQ ID NO:32, S12A2-S1 PCR primer
SEQ ID NO:33, S12A2-S2 PCR primer
SEQ ID NO:34, S12A2-A1 PCR primer
SEQ ID NO:35, S12A2-A2 PCR primer
SEQ ID NO:36, pQE61-f primer
SEQ ID NO:37, pQE61-r primer
SEQ ID NO:38, T128-F PCR Primer
SEQ ID NO:39, T128-R PCR Primer
SEQ ID NO:40, PhF3H-ClaI PCR Primer
SEQ ID NO:41, ThF3H-SalI1 PCR Primer
SEQ ID NO:42, ThF3H-SalI2 PCR Primer
SEQ ID NO:43, TpCHI-SalI PCR Primer
SEQ ID NO:44, TpCHI-XbaI1 PCR Primer
SEQ ID NO:45, TpCHI-XbaI2 PCR Primer
SEQ ID NO:46, PacI-FseIF adapter inserted in a vector
SEQ ID NO:47, PacI-FseIR adapter inserted in a vector
SEQ ID NO:48, M13RV PCR Primer
SEQ ID NO:49, BamHI-CHI-F PCR Primer
SEQ ID NO:50, Sal-CHI-R PCR Primer
SEQ ID NO:51, Sal-CHI-F PCR Primer
SEQ ID NO:52, EcoRI-CHI-R PCR Primer
SEQ ID NO:53, YCy3-12P1 PCR Primer
SEQ ID NO:54, YCy3-12P2 PCR Primer
SEQ ID NO:57, EcoFseI Primer
SEQ ID NO:58, EcoFseR Primer
SEQ ID NO:59, HinFseR Primer
SEQ ID NO:60, HinFse3 Primer

The invention claimed is:

1. An isolated polynucleotide encoding a protein comprising the amino acid sequence described in SEQ ID NO: 2 or an amino acid sequence having 1-30 amino acid substitutions in the amino acid sequence of SEQ ID NO: 2 and having an activity to transfer sugar to position 2' of chalcones.

2. A vector comprising the isolated polynucleotide according to claim 1.

3. A host cell transformed with the vector according to claim 2.

4. A method for producing a protein, which comprises culturing or growing the host cell according to claim 3, and collecting said protein having an activity to transfer sugar to position 2' of chalcones from said host cell.

5. A protein obtained by the method according to claim 4.

6. A plant into which the isolated polynucleotide according to claim 1 has been introduced, or a plant which is a progeny of said plant, or tissue of said plant.

7. A cut flower collected from the plant according to claim 6.

8. A plant in which flower color has been modified by introducing and expressing the isolated polynucleotide according to claim 1 in the plant, and a plant which is a progeny of said plant.

9. The plant according to claim 8, wherein a modified flower color is yellow.

* * * * *